(12) United States Patent
Rose et al.

(10) Patent No.: US 9,511,195 B2
(45) Date of Patent: Dec. 6, 2016

(54) SUBCUTANEOUS HYDRATION SYSTEM, METHOD, AND DEVICE

(71) Applicant: University Hospitals Case Medical Center, Cleveland, OH (US)

(72) Inventors: Johnie Rose, Cleveland, OH (US); Conor P. Delaney, Cleveland, OH (US)

(73) Assignee: University Hospitals of Cleveland, Cleveland, OH (US)

( * ) Notice: Subject to any disclaimer, the term of this patent is extended or adjusted under 35 U.S.C. 154(b) by 0 days.

(21) Appl. No.: 14/211,006

(22) Filed: Mar. 14, 2014

(65) Prior Publication Data

US 2014/0276410 A1    Sep. 18, 2014

Related U.S. Application Data

(60) Provisional application No. 61/793,200, filed on Mar. 15, 2013.

(51) Int. Cl.
*A61M 5/20* (2006.01)
*A61M 5/46* (2006.01)
*A61M 5/42* (2006.01)
*A61M 5/158* (2006.01)

(52) U.S. Cl.
CPC ............... *A61M 5/46* (2013.01); *A61M 5/422* (2013.01); *A61M 5/425* (2013.01); *A61M 2005/1585* (2013.01)

(58) Field of Classification Search
CPC .................................. A61M 5/46; A61M 5/42
USPC .................... 604/112–118, 135–139, 164.01, 164.02, 604/250, 180, 174, 110, 151
See application file for complete search history.

(56) References Cited

U.S. PATENT DOCUMENTS

| | | | |
|---|---|---|---|
| 4,790,823 A | 12/1988 | Charton et al. | |
| 5,199,952 A | 4/1993 | Marshall, Sr. et al. | |
| 5,776,106 A * | 7/1998 | Matyas | 604/180 |
| 7,670,314 B2 | 3/2010 | Wall et al. | |
| 2003/0233070 A1 | 12/2003 | De La Serna | |

(Continued)

OTHER PUBLICATIONS

Revised Drawing submitted for U.S. Appl. No. 10/594,043.*
International Search Report for PCT/US2014/027373 dated Aug. 1, 2014.

*Primary Examiner* — Theodore Stigell
*Assistant Examiner* — Tiffany Legette
(74) *Attorney, Agent, or Firm* — Richard M. Klein; Fay Sharpe LLP

(57) ABSTRACT

Systems, methods, and devices for providing subcutaneous hydration are disclosed. A system for providing subcutaneous hydration may include an infusion bag including a hydration fluid, a tubing removably connected to the infusion bag, a squeezable bulb at least partially encompassing the tubing for at least one of flushing and priming the tubing, and a deployment device including an integrated needle which is operative provide subcutaneous hydration through the needle. A deployment device for subcutaneous hydration includes a base may include a needle aperture, a spring-loaded barrel attached the base and including a needle, and a firing mechanism within the barrel for deploying the needle from the barrel and further operative to project the needle through the aperture only when a tent of skin has been raised within the aperture for injection. A method for providing subcutaneous hydration may include steps necessary to operate the systems and devices for subcutaneous hydration.

11 Claims, 31 Drawing Sheets

(56) References Cited

U.S. PATENT DOCUMENTS

| | | | |
|---|---|---|---|
| 2004/0049155 A1* | 3/2004 | Schramm | 604/110 |
| 2004/0162521 A1* | 8/2004 | Bengtsson | 604/136 |
| 2005/0101933 A1* | 5/2005 | Marrs et al. | 604/506 |
| 2008/0039794 A1* | 2/2008 | Kornerup et al. | 604/136 |
| 2009/0299287 A1* | 12/2009 | Carson et al. | 604/113 |
| 2011/0106022 A1* | 5/2011 | Jackson et al. | 604/290 |
| 2011/0313362 A1* | 12/2011 | Bierman | 604/180 |
| 2011/0319860 A1 | 12/2011 | Williamson et al. | |

* cited by examiner

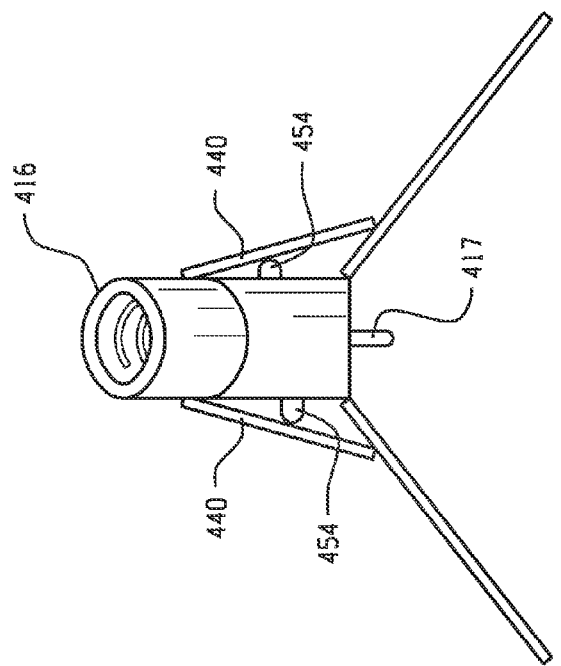
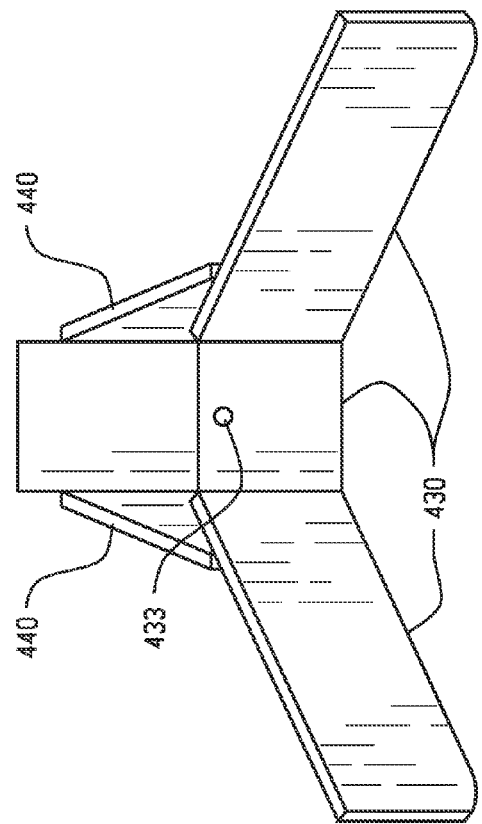
Fig. 25(b)
Fig. 25(a)

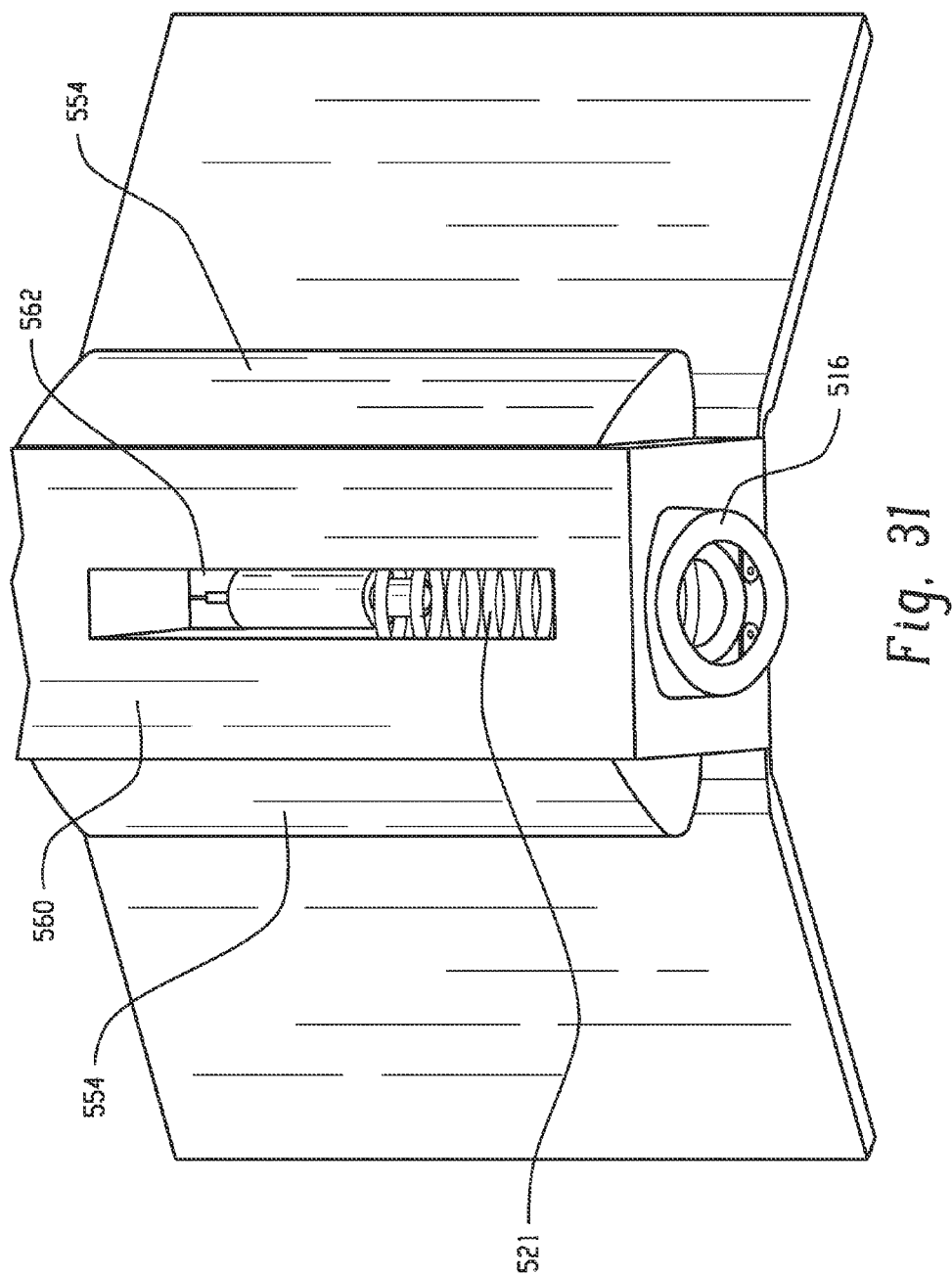

SUBCUTANEOUS HYDRATION SYSTEM, METHOD, AND DEVICE

CROSS-REFERENCE TO RELATED APPLICATIONS

This application claims priority to U.S. Provisional Patent Application Ser. No. 61/793,200, filed on March 15. The entirety of that application is fully incorporated by reference herein.

BACKGROUND

The present disclosure relates to systems, methods, and devices for providing subcutaneous hydration. Generally, the system may be used to provide subcutaneous hydration in a cost effective, integrated, and simple manner that is performable by non-clinically trained administrators. Methods to produce a deployment device and to provide subcutaneous hydration are also disclosed. The device may be an integrated unit for delivering subcutaneous hydration to patient in safe, cost-effective, durable, and/or less risky manner.

Generally practiced methods for rehydrating patients who suffer from severe dehydration include intravenous (IV) rehydration and oral rehydration therapy (ORT). IV rehydration provides a fast aqueous drip rate and is preferable when treating severely dehydrated patients. However, IVs also require individuals with a high level of skill for their set up and administration. By contrast, oral rehydration therapy does not require a high degree of skill to administer, yet also provides a must slower rehydration effect.

Often, individuals in remote parts of the developing world either lack access to formal medical care where intravenous fluids can be administered, or face significant delay and transit times before obtaining medical care. Over 1.5 million children die annually due to diarrhea despite increasingly effective implementation of programs to increase access to oral rehydration solutions. Accordingly, the situation inevitably arises where oral rehydration therapy does not provide a sufficient rehydration rate for a specific patient, e.g. one who is overly dehydrated or suffering from emesis, while individuals with the skill necessary to set up IV rehydration on the patient are not readily available. In this case, an intermediary measure may be a more appropriate solution. This measure will not replace IV or ORT, but rather provide a practical bridge therapy which may help avert circulatory collapse.

One secondary or intermediary rehydration method involves subcutaneous, as opposed to intravenous, delivery of rehydrating fluids. Such devices should be easier to administer as no needle puncture of human veins is required. The set up time should also be much quicker, and the cost necessarily lower. Local clinically-trained personnel would not be required to administer this intermediary measure.

Current subcutaneous rehydration devices, e.g. a butterfly needle attached to a saline bag with an attached drip set, have a number of recognized limitations. First, they do not provide enough failsafe guidance for non-clinically trained administrators of self-administrating patients. While subcutaneous injection does not puncture human veins, it may can cause unnecessary pain when the injection is performed improperly, e.g., using the wrong injection angle, depth, or injection site. Second, these devices may also not be integrated well enough for non-clinically trained administrators to provide facile treatment without confusion, delay, and/or impaired effectiveness.

It would be desirable to provide systems, methods, and devices for self-contained subcutaneous hydration device which may be used by minimally-trained caregivers, which are the predominate type of caregivers in remote situations. It would also be desirable to provide durable, easy-to-use systems, methods, and devices for administering parenteral fluids using a subcutaneous temporizing measure when oral rehydration therapies are insufficient and IV fluids will be delayed or are unavailable. Such subcutaneous measure should provide sufficient guidance as to reduce the pain experienced by a patient when administered by non-clinically trained technicians. Such measures should also be well integrated to reduce confusion and loss of effectiveness, while also being cost effective for proliferate use in economically depressed regions, trauma or battlefield situations, and emergency and disaster relief.

BRIEF DESCRIPTION

Disclosed in various embodiments are systems for providing subcutaneous hydration including an infusion bag having a hydration fluid; and tubing removably attached to the infusion bag which provides the hydration fluid to a deployment device attached to the tubing. The tubing is attached to a slidable lure within the deployment device at a connection point.

The lure may be removably attached to a needle operative to deliver the hydration fluid to a subcutaneous region of a patient. An adhesive base can be placed between the subcutaneous region and the deployment device. The adhesive base may include an emulsion of at least one of prilocaine and lidocaine local anesthetic. In particular embodiments, the adhesive base includes at least one of polypropylene and tegaderm.

The deployment device may comprise an acrylic sheet.

Also disclosed in embodiments are deployment devices for subcutaneous hydration which include a wedge back attached to a wedge ramp which props the wedge back at a predefined angle, a slider track within the wedge ramp, a slider removably attached to the slider track and operative to translate along the wedge ramp, and a lure including a removably attached needle. The lure is at least partially encompassed by and directed by the movement of the slider into a dermal region injection site.

In particular embodiments, the wedge back and wedge ramp are made from acrylic and are attachable by adhesive. The predefined angle can be between 10 and 30 degrees. The needle is generally directed by the slider into a subcutaneous region and is operative to deliver hydration fluid to the subcutaneous region.

In other embodiments, the deployment device further includes a hole for at least one of inserting and translating the lure through the wedge back.

Also disclosed in several embodiments, are methods for forming a low-cost acrylic deployment device that include: forming first, second, and third portions of acrylic sheet from acrylic sheet stock, generating a slider track in the first sheet portion, cutting a cube out of acrylic sheet stock to form a slider, cutting at least two rectangular sections from the slider for interfacing the slider with the slider track, cutting a hollow cylinder out of the slider for receiving a lure, and forming a needle carriage from the first, second, and third acrylic sheet portions.

The needle carriage can be formed by gluing the acrylic sheet portions together. An angle of approximately 30 degrees may be maintained between acrylic sheet portions forming the smallest angle in the needle carriage.

Additionally disclosed herein are different embodiments of a system for providing subcutaneous hydration that include: an infusion bag including a hydration fluid, a tubing removably connected to the infusion bag, a squeezable bulb at least partially encompassing the tubing for at least one of flushing and priming the tubing, and a deployment device including an integrated needle. The deployment device is connected to the tubing and is operative to provide subcutaneous hydration through the needle.

The squeezable bulb may include a one-way valve. The tubing can be pre-connected to the infusion bag.

The present disclosure also relates to deployment devices for subcutaneous hydration that include: a base including a needle aperture, a spring-loaded barrel attached to the base and including a needle, and a firing mechanism within the barrel for deploying the needle from the barrel. The firing mechanism is operative to project the needle through the aperture only when a tent of skin has been raised within the aperture for injection.

The deployment device may further include at least one actuator attached to the barrel for regulating a needle slot. The deployment device may further include at least one wing attached to the base for engaging the at least one actuator. The at least one wing can engage the at least one actuator by gripping or pinching the at least one wing against the barrel.

The base may include at least one of an antimicrobial material and a waterproof adhesive. The barrel may at least partially encompass a tubing operative to provide hydration fluid to the needle.

The deployment device may further include a casing attached to the base which at least partially encompasses the barrel. The casing can include a slider track for retracting the needle within the spring-loaded barrel. The needle aperture may be oblong to accommodate needle movement while the needle is at least partially stabilized by the barrel.

The deployment device may further include an adhesive located on the base (530). The adhesive can be impregnated with an emulsion of at least one of prilocaine and lidocaine local anesthetic.

In still other embodiments disclosed herein are methods for providing subcutaneous hydration that include: hanging an infusion bag containing infusion liquid above a patient, spiking the infusion bag by sliding a pre-connected tube towards the bag and twisting to lock, squeezing a bulb encompassing the tube to prime the tube, and pinching wings together on a deployment device until a click is felt indicating that a tent of skin has been isolated, wherein a needle is automatically deployed and subcutaneous hydration is provided to the patient.

The wings are slowly released to allow them to return to a nearly-flat position. A slider can be translated until locked in order to withdraw the needle from the patient.

These and other non-limiting aspects of the present disclosure are further discussed herein.

BRIEF DESCRIPTION OF THE DRAWINGS

The following is a brief description of the drawings, which are presented for the purposes of illustrating the exemplary embodiments disclosed herein and not for the purposes of limiting the same.

FIG. 25 is a bottom and rear view of a deployed state of the deployment device according to FIG. 24.

FIG. 30 is a conceptual drawing showing the potential movement of the needle within the oblong needle aperture space in the deployment device according to FIG. 27.

FIG. 31 is a top cutaway view of the 3D model of the deployment device according to FIG. 27 prominently displaying a slider track for disengaging the needle after deployment.

DETAILED DESCRIPTION

Figure 1:
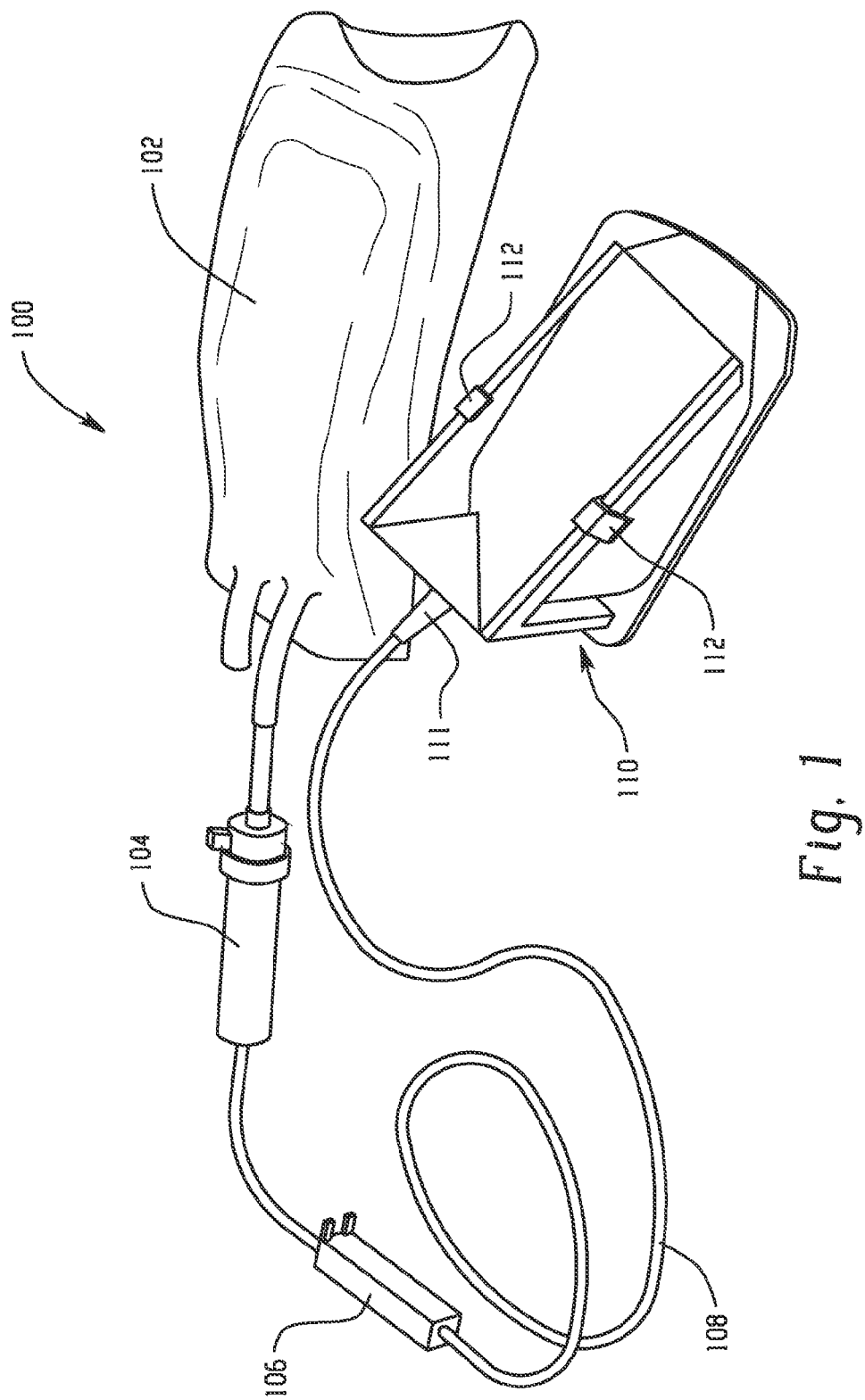
FIG. 1 is an overview photograph of a system for providing subcutaneous hydration.

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

With reference to FIG. 1, a first exemplary system 100 for subcutaneous hydration includes an infusion bag 102 attached to a drip chamber 104. The infusion bag 102 may contain a measured amount, e.g., 500 mL or more, of saline solution or any other isotonic crystalloid sterile hydration fluid known to one having ordinary skill in the art. The infusion bag 102 may be placed above the head of a patient (not pictured) so that gravity aids the outward flow of hydration fluid. The drip chamber 104 allows for a constant drip or flow rate to be established. A tubing 108 extends from the drip chamber 104 and channels the flow of hydration fluid to a deployment device 110. A roller clamp 106 acts to selectively close or open the flow of hydration fluid through the tubing 108 based on the decision of a rehydration fluid administrator. The tubing 108 interfaces with the deployment device 110 at a tubing-lure-needle-connection 111. Optional slider locks 112 affect the operability of the deployment device 110, which will be described in further detail in FIG. 2.

Figure 2:
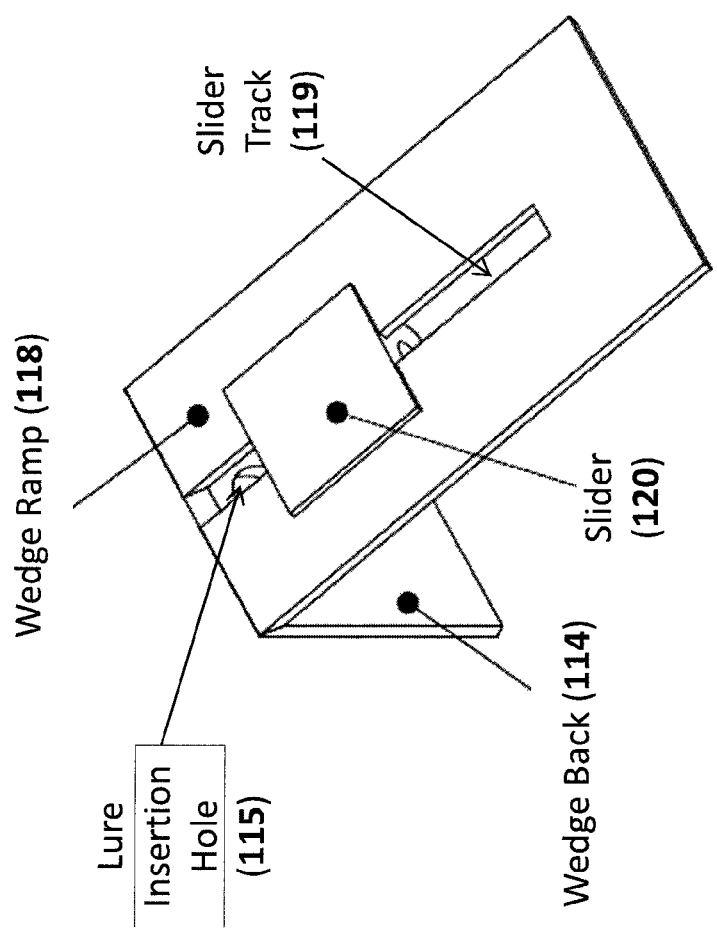
FIG. 2 is a perspective drawing of a deployment device for subcutaneous hydration according to a first exemplary embodiment.
Figure 3:
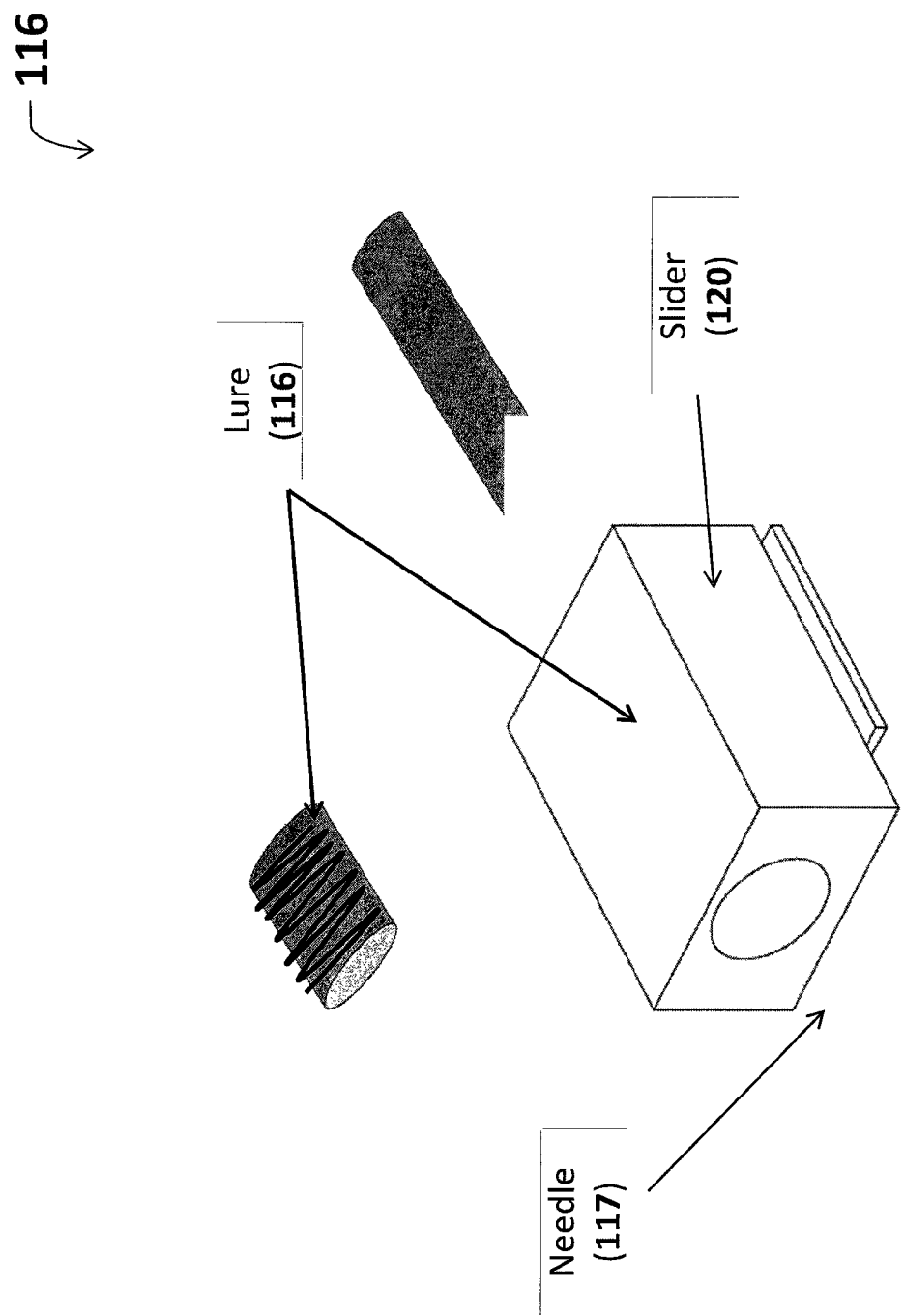
FIG. 3 is a perspective drawing of a lure from the deployment device according to FIG. 2.

With reference to FIG. 2 and FIG. 3, the deployment device 110 according to a first exemplary embodiment is comprised of a wedge back 114 which is connected to a wedge ramp 118 at a predefined angle. The wedge ramp 118 includes a slider track 119 which enables a slider 120 to translate along the plane of the wedge ramp 118. The wedge back 114 includes a lure insertion hole 115 (view partially blocked) for inserting a lure 116 which may be attached to a needle 117. The lure also travels within the slider 120, where the slider 120 is removably attachable to the wedge ramp via the slider track 119.

The wedge back 114, wedge ramp 118, and slider 120 may be made of acrylic or other low cost material. The lure 116 may be a catheter lure that is approximately 0.75 inches in diameter. The needle 117 may be a 0.5 inch in length needle with a 24 gauge diameter.

Figure 4:
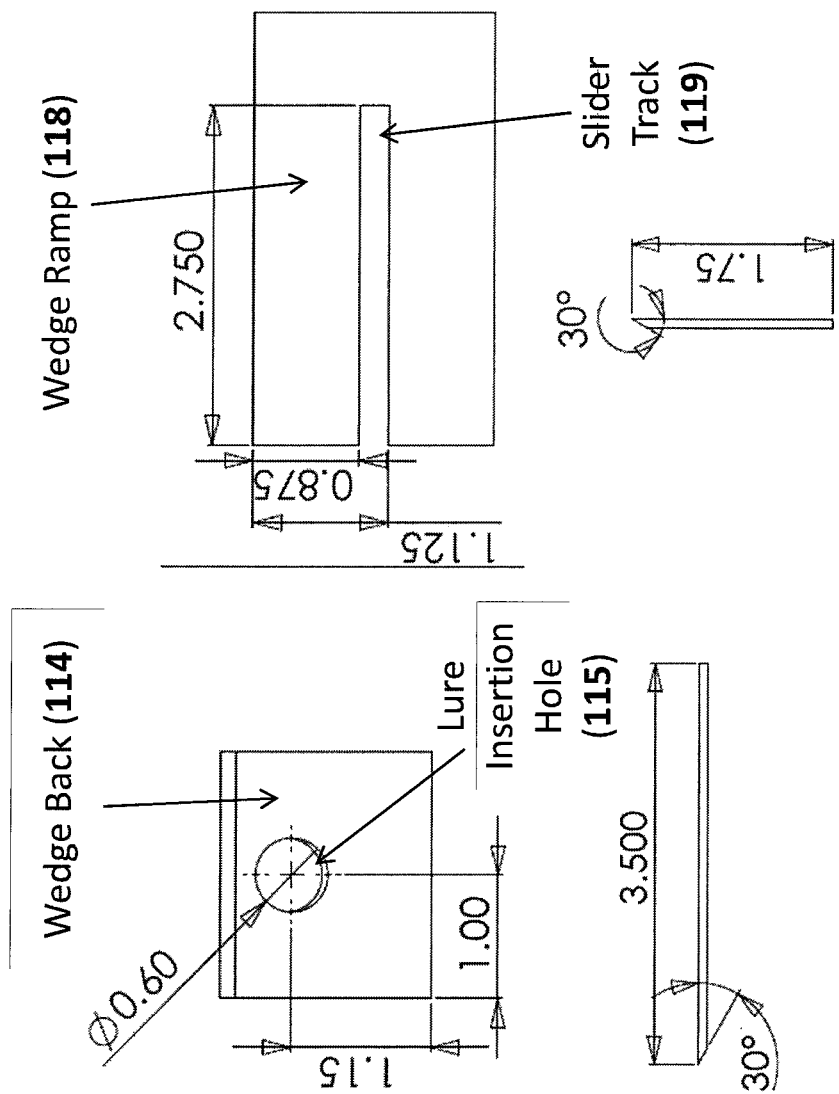
FIG. 4 is a technical diagram of the deployment device according to FIG. 2 which provides demonstrative dimensional features.

With reference to FIG. 4, the predefined angle between the wedge back 114 and wedge ramp 118 and exemplary length and width dimensions for the wedge back 114, lure insertion hole 114, and wedge ramp 118 according to one embodiment of the deployment device 110 are illustrated in FIG. 4. It should be noted that while 30 degree angles are indicated in FIG. 4, angles between approximately 10 and 30 degrees is also contemplated.

Figure 5:
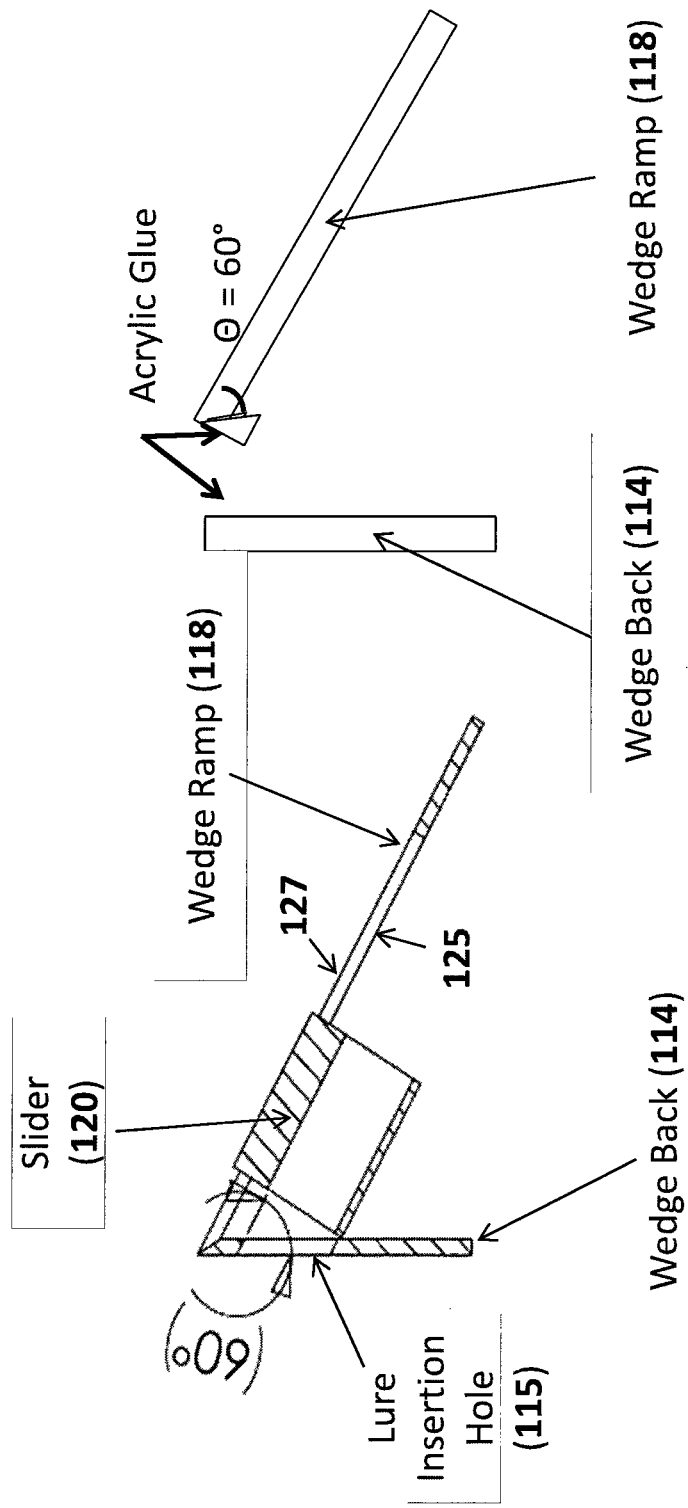
FIG. 5 is a drawing of the interface between a wedge back and a wedge ramp from the deployment device according to FIG. 2.
Figure 6:
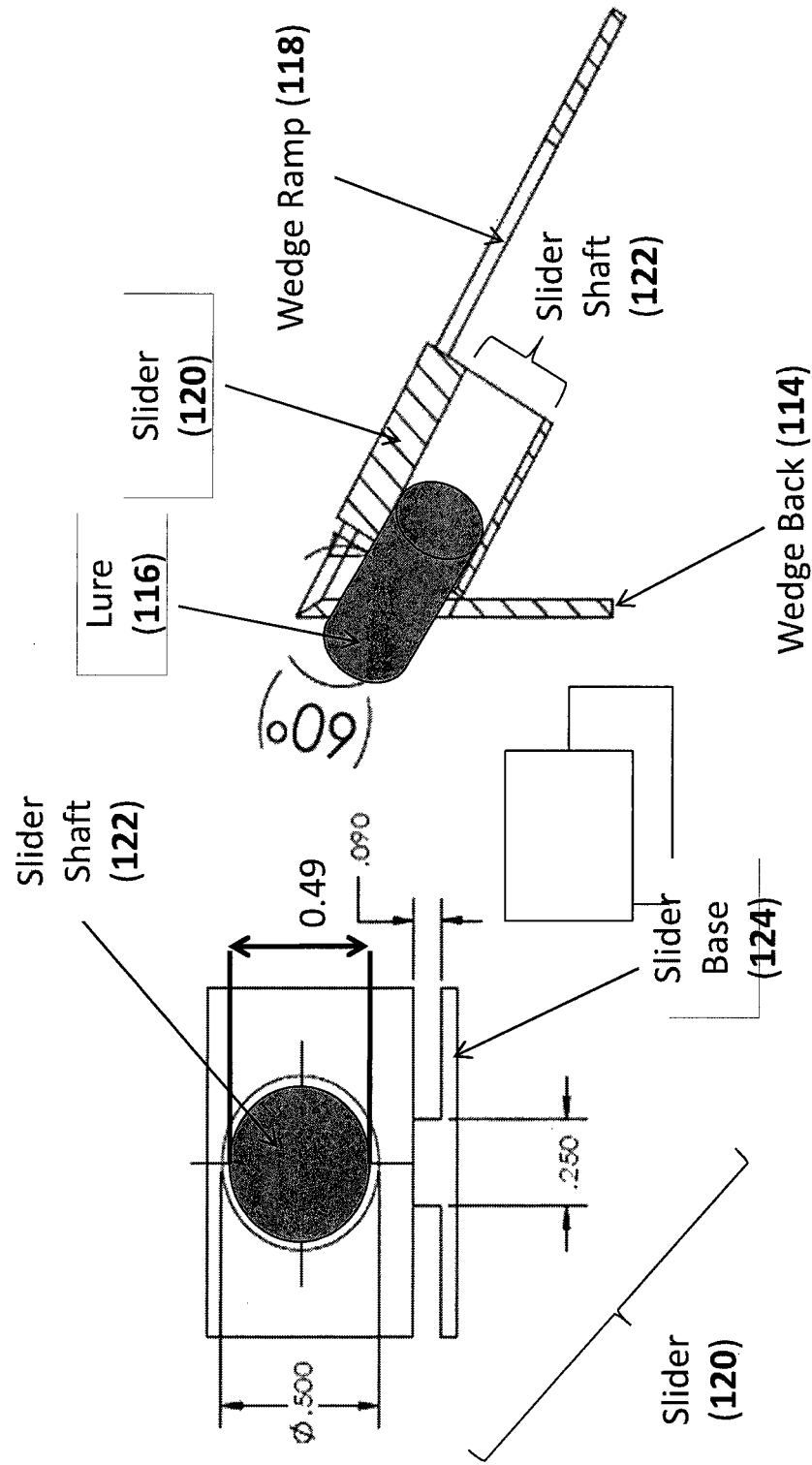
FIG. 6 is a drawing of the interface between a slider and a lure of the deployment device according to FIG. 2.

With reference to FIG. 5, the interface between the wedge back 114 and wedge ramp 118 is illustrated. Wedge back 114 and wedge ramp 118 may intersect at approximately a 60 degree angle and may be further be held together by acrylic glue. Other adhesives may be used as known by one having ordinary skill in the art. The majority of slider 120 is located on the underside 125 of wedge ramp 118 once fit within the slider track 119 (not shown).

Figure 7:
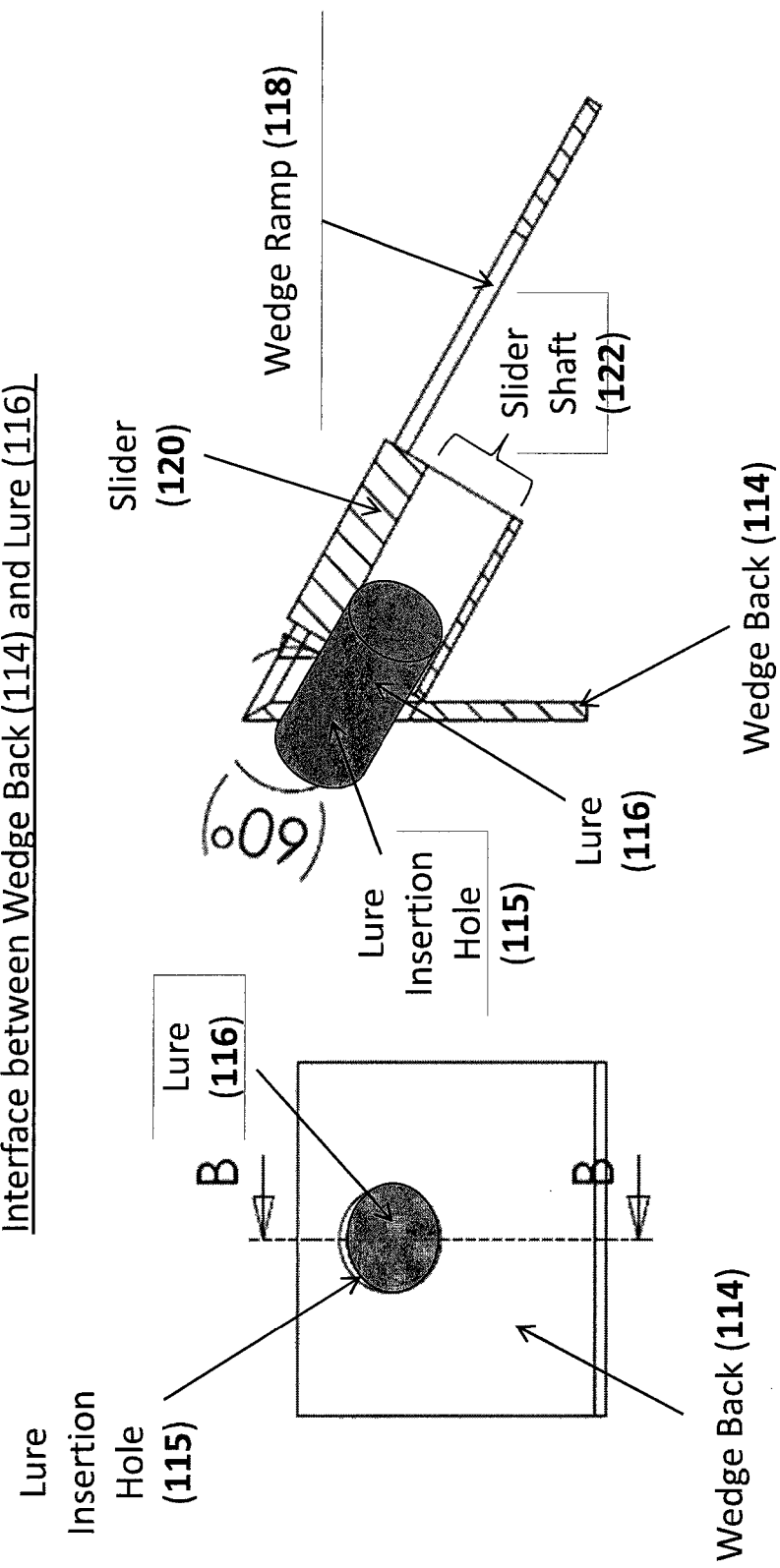
FIG. 7 is a drawing of the interface between the wedge back and the lure of the deployment device according to FIG. 2.

With reference to FIG. 7, the interface between the slider 120 and the lure 116 reveals that the slider 120 may both encompass the lure 116 within shaft 122 and also direct the lure 116 in and out of lure insertion hole 115 in wedge back 114 as slider 120 translates along the tracks 119 cut into the wedge ramp 118.

Figure 8:
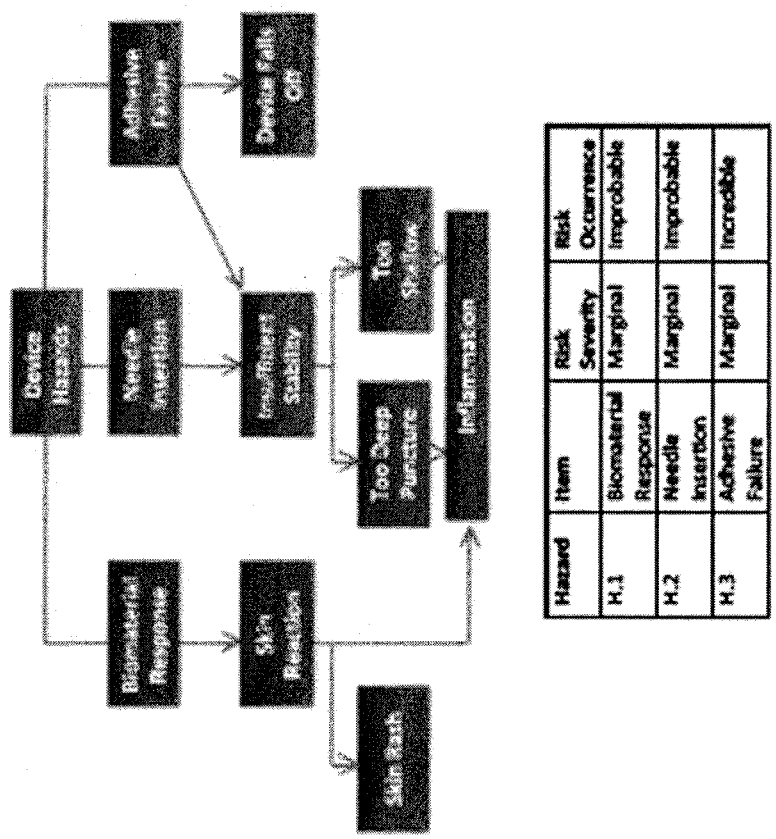
FIG. 8 is a flow chart of the potential hazards presented by subcutaneous deployment devices.

With reference to FIG. 8, there are three classes of common hazards associated with deployment device 110 and similar subcutaneous hydration devices. These risks generally include (1) unfavorable biomaterial responses, such as skin reaction, skin rash, and inflammation, (2) unstable needle insertion, whether too deep, two shallow, or at an improper angle, as well as (3) adhesive failures, which means the device may fall off the skin or fail to properly mount during deployment. Considering these inherent risks for subcutaneous delivery devices, device 110 may incorporate novel biomaterials of novel combinations of biomaterials that minimize reactions and/or rashes. Device 110 may further use a predefined injection angle and or other mechanisms which ensure that puncture is not too deep or shallow even when administered by non-clinically trained technicians. Device 110 may additionally use an appropriate kind and number of adhesive materials to maintain consist mounting of device 110 during injection and administration of hydration fluids.

Figure 9:
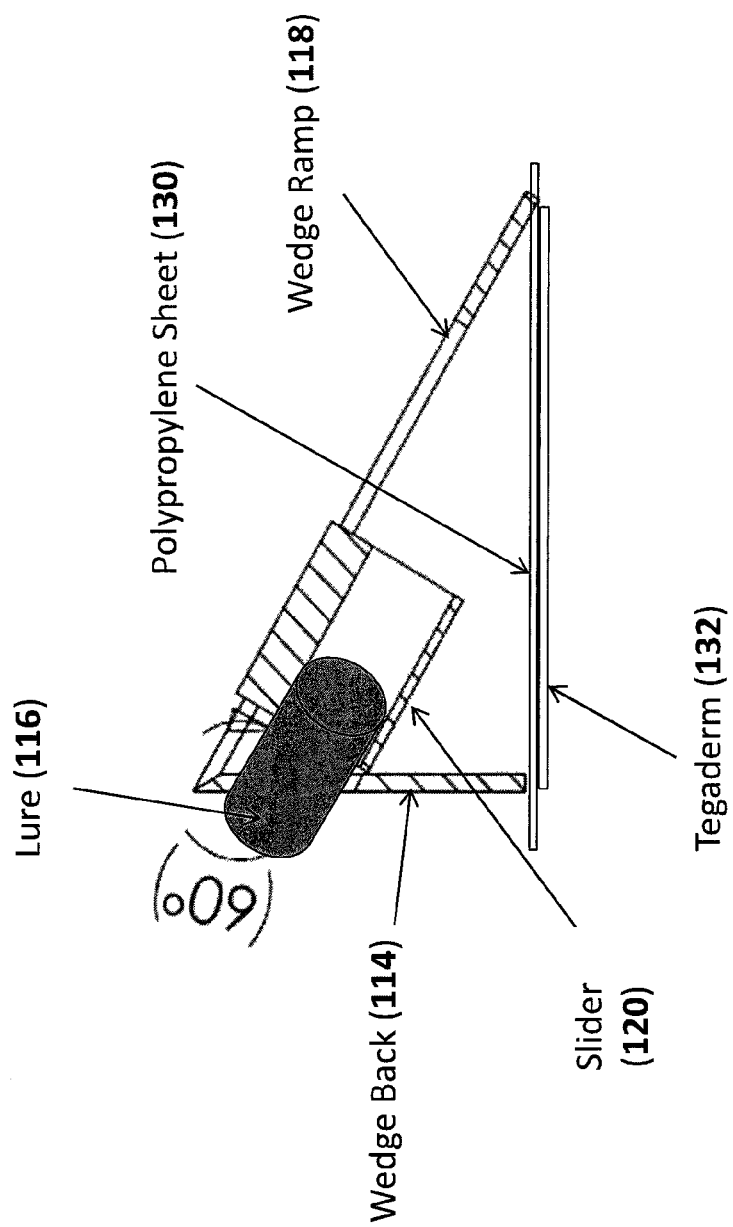
FIG. 9 is a drawing of the deployment device according to FIG. 2 provided with additional polypropylene sheet and tegaderm adhesive.

With reference to FIG. 9, the deployment device 110 may be also be envisioned as resting upon a polypropylene sheet 130 with tegaderm adhesive 132 subsequently below for adhering to human skin. These antimicrobial and otherwise biocompatible materials 130, 132 allow for the deployment device 110 to be well adhered to the skin, and therefore promote injection stability, while also not causing an adverse bodily reaction.

Figure 10:
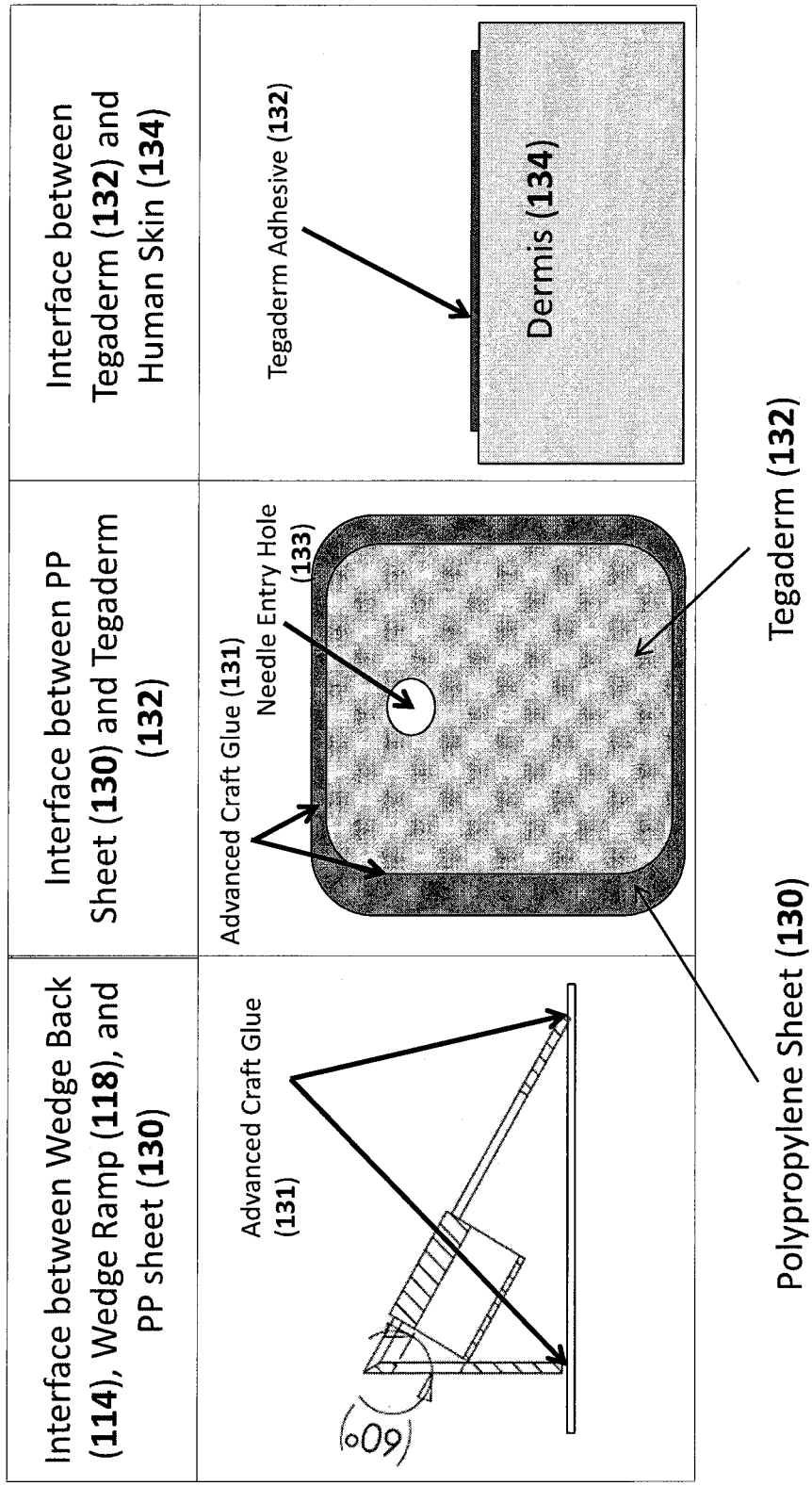
FIG. 10 is a drawing of (1) the interface between the wedge back, wedge ramp, and polypropylene sheet, (2) the interface between the polypropylene sheet and the tegaderm adhesive, and (3) the interface between the tegaderm adhesive and human skin or dermis, all interfaces from the deployment device according to FIG. 2.
Figure 11:
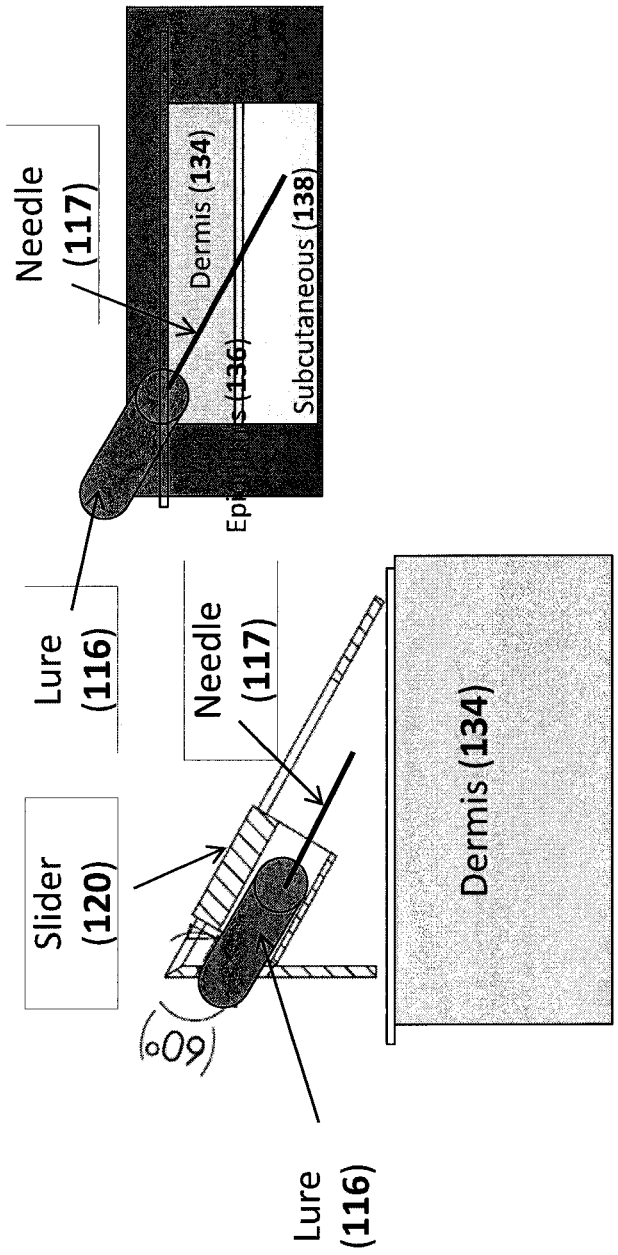
FIG. 11 is a drawing of the interface between a subcutaneous layer of human skin and a needle of the deployment device according to FIG. 2.
Figure 12:
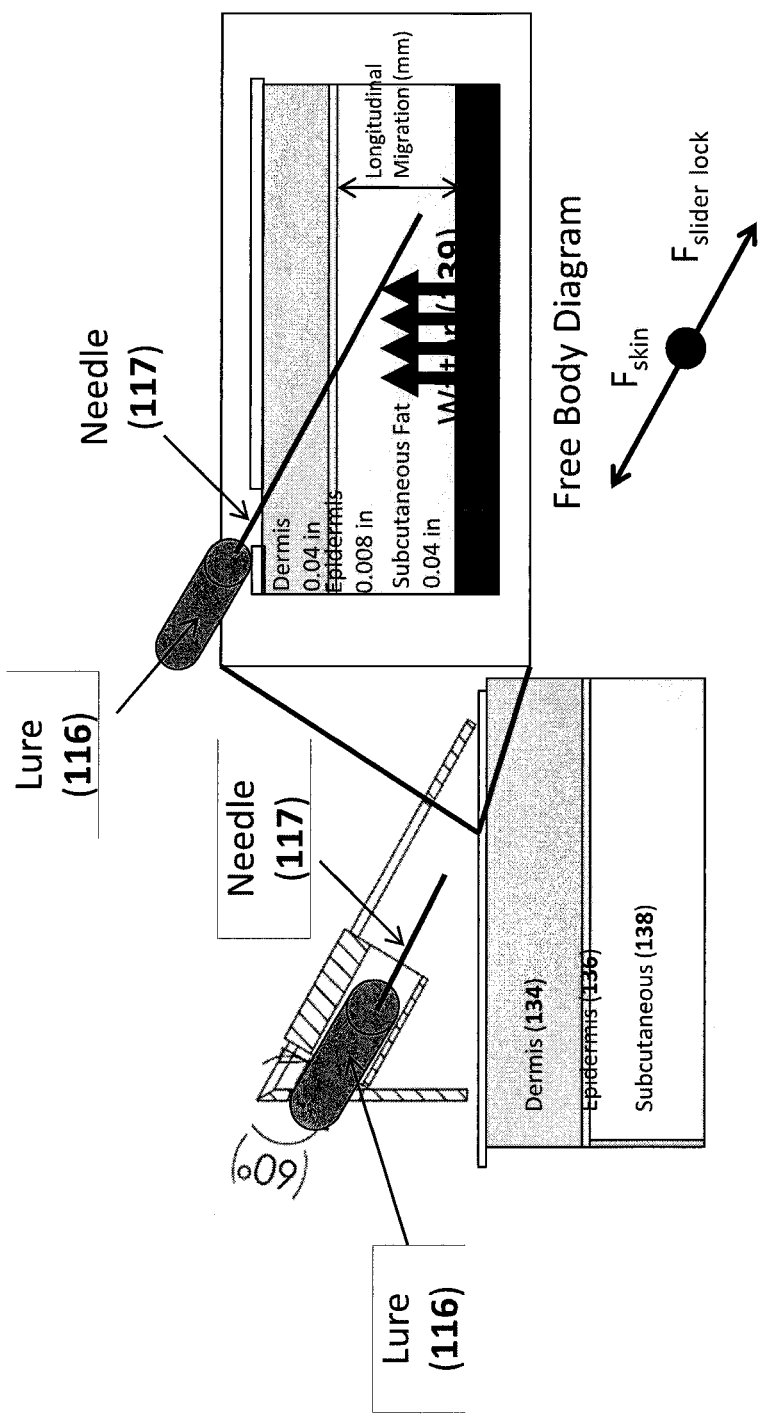
FIG. 12 is a drawing illustrating the penetration of the needle from the deployment device according to FIG. 2 into the subcutaneous region.

With reference to FIGS. 10-12, the wedge back 114 and wedge ramp 118 may be adhered to the polypropylene sheet 130 referenced in FIG. 9 by advanced craft glue 131, acrylic glue, or other similar adhesives known to one having ordinary skill in the art. In order for a needle 117 attached to the lure 116 to be inserted into a subcutaneous region of human skin (shown in FIGS. 11-12), the needle 117 may have to pass through both the polypropylene sheet 130 and tegaderm adhesive 132. Accordingly, a needle entry hole 133 may be fashioned in the sheet/adhesive 130, 132 at the point of needle insertion into the skin to facilitate injection. Tegaderm adhesive 132 may still be used for stabilizing the deployment device 110 on the dermis 134 without blocking insertion of needle 117 through use of the entry hole 133.

With reference to FIG. 11, the needle 117 is inserted further into the dermis 134 by translating the slider 120 (and encompassed lure 116) towards the dermis 134. The needle 117 will pass through a thin epidermis layer 136 before entering the subcutaneous layer 138 of skin.

With reference to FIG. 12, FIG. 1, and FIG. 2, once the lure 116 and associated needle 117 have penetrated into the subcutaneous layer 138, the lure/needle 116, 117 may be locked into position by locking the slider 120 with at least one slider lock 112. The slider lock 112 places a downward force ($F_{slider\ lock}$) on the slider 120, which also experiences a repelling force from the skin ($F_{skin}$). As water is expelled into the subcutaneous later 138, the skin force $F_{skin}$ becomes larger, and may overcome $F_{slider\ lock}$, which tends to vary the position of the needle 117 within the subcutaneous layer 138. The distance of potential needle 117 migrations within the subcutaneous layer 138 has been indicated in FIG. 12 with a longitudinal migration distance.

Figure 13:
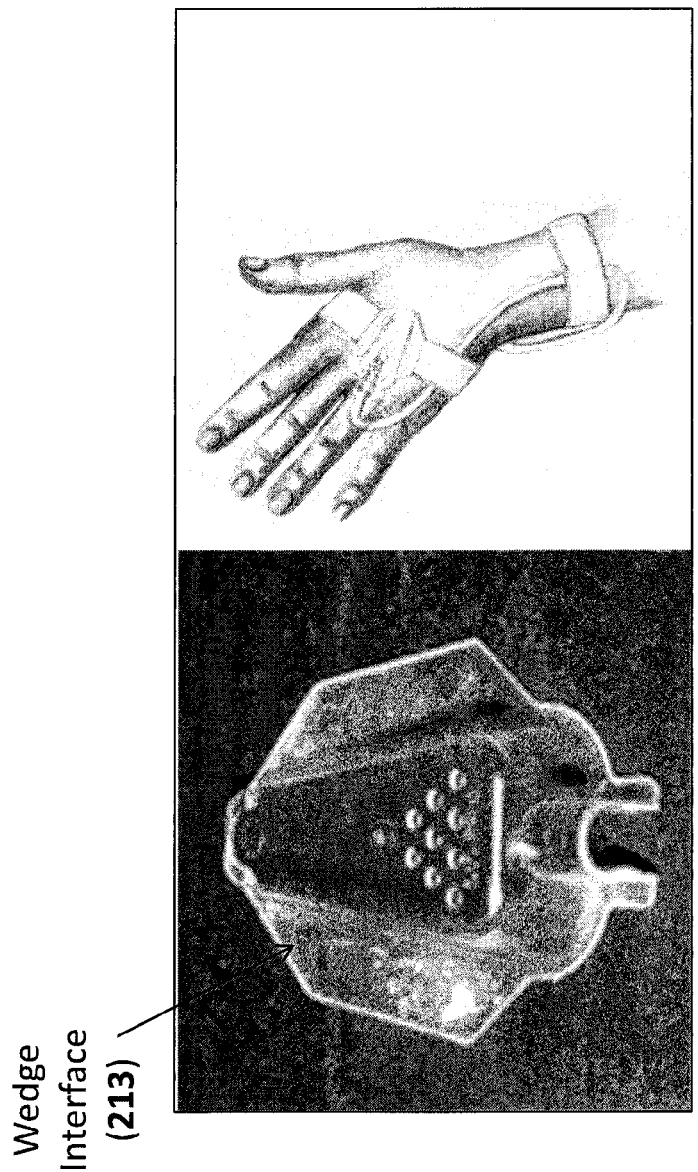
FIG. 13 is a photograph and drawing of a deployment device for subcutaneous hydration according to a second exemplary embodiment.
Figure 14:
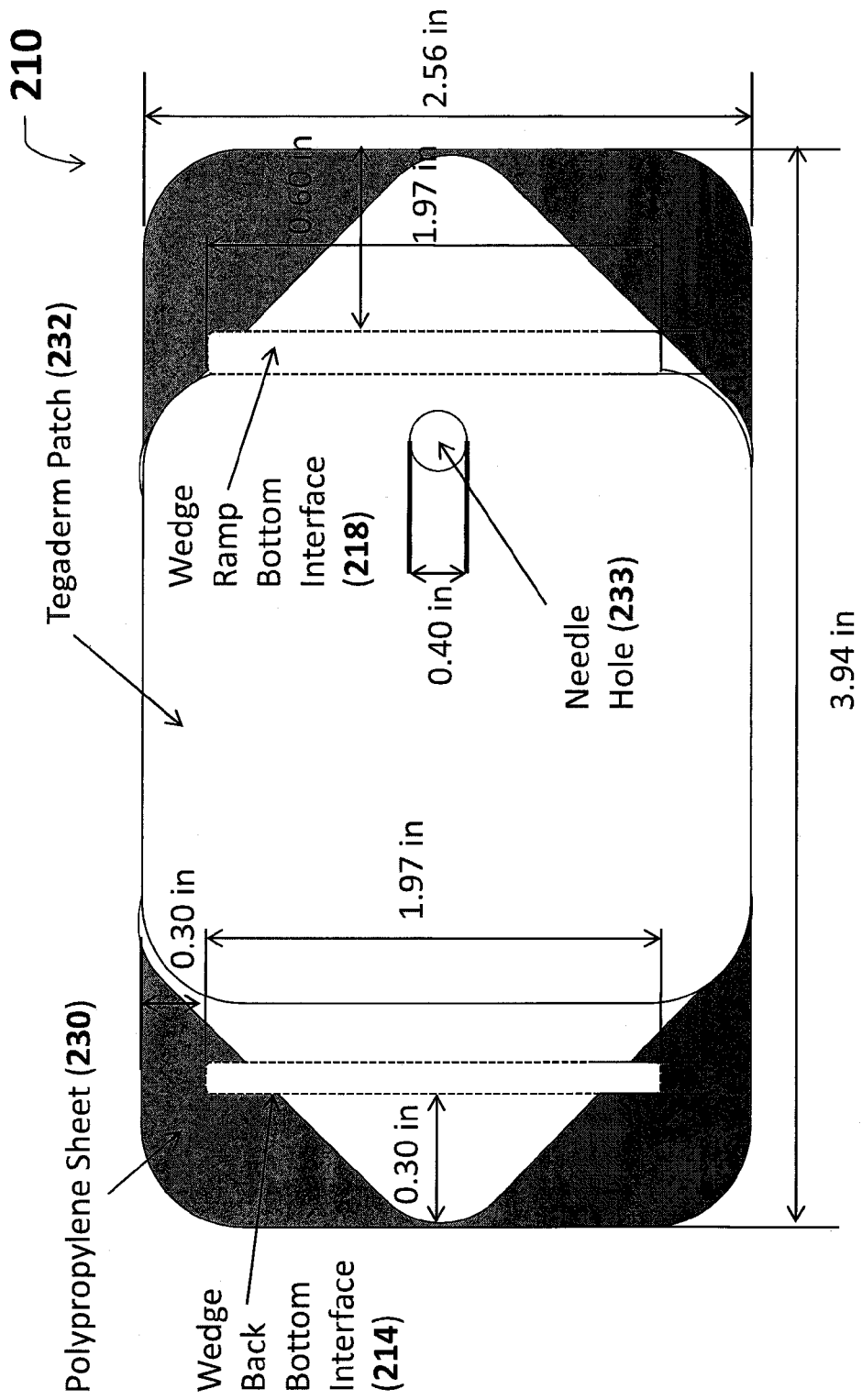
FIG. 14 is a technical diagram of the deployment device according to FIG. 13 which provides demonstrative dimensional features.

With reference to FIG. 13 and FIG. 14, a deployment device 210 according to a second exemplary embodiment is a smaller device 210 which can fasten to a patient's hand or other small region. The deployment device 210 employs similar injection principles as device 210 however is manufactured differently to provide a smaller integrated wedge interface 213, made up of a wedge back bottom interface 214 and wedge ramp bottom interface 218. The interfaces are placed upon a polypropylene sheet 230 with and tegaderm patch 132, which may be non-rectangular, or take on other shapes as necessary for adhering to different areas of skin. A needle hole 233 provides a point of entry for a needle 217 (not shown) through the polypropylene sheet 230 and tegaderm patch 232 into the skin.

Figure 15:
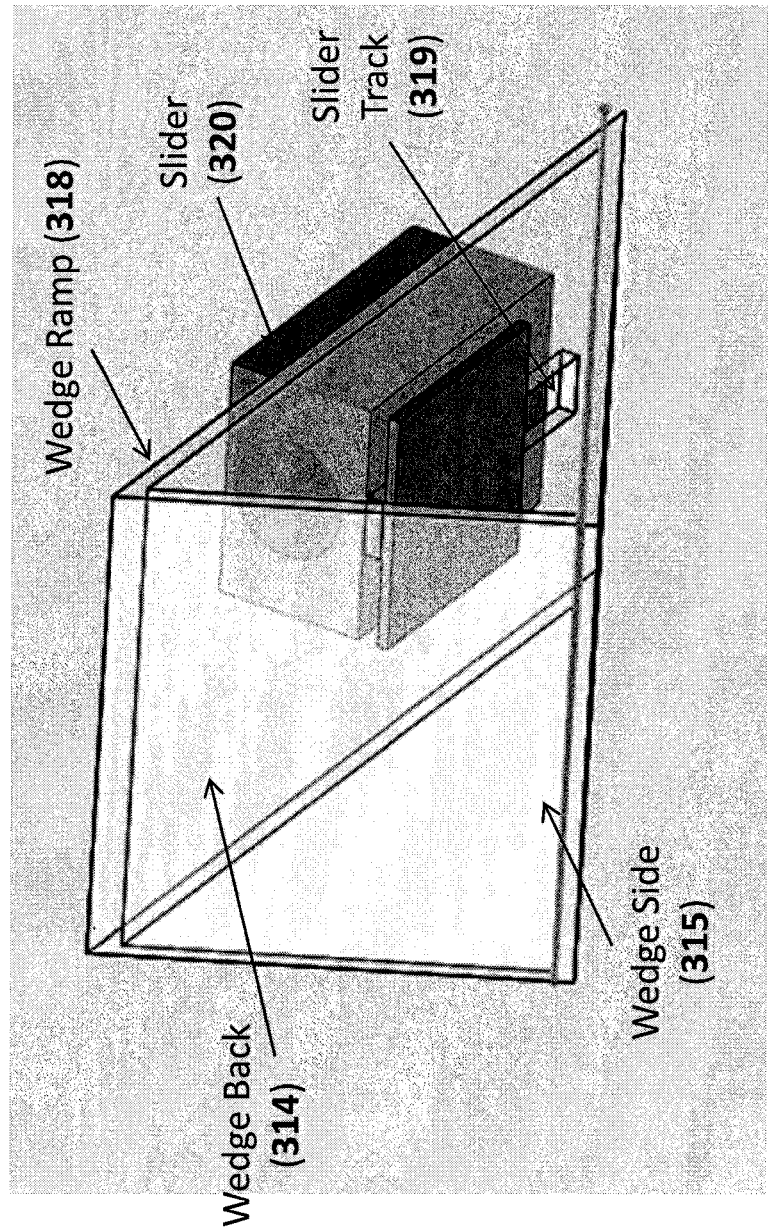
FIG. 15 is a perspective drawing of a deployment device for subcutaneous hydration according to a third exemplary embodiment of the invention.

With reference to FIG. 15, a deployment device 310 according to a third exemplary embodiment includes a three wedge pieces: a wedge back 314, wedge side 315, and wedge ramp 318. A slider 320 translates along a slider track 319 cut into the wedge ramp 318, where the track 319 which is relatively smaller than slider track 119 from deployment device 110. All wedge pieces 314, 315, 318, may be constructed from acrylic or other low cost materials as are known to one having ordinary skill in the art.

Figure 16:
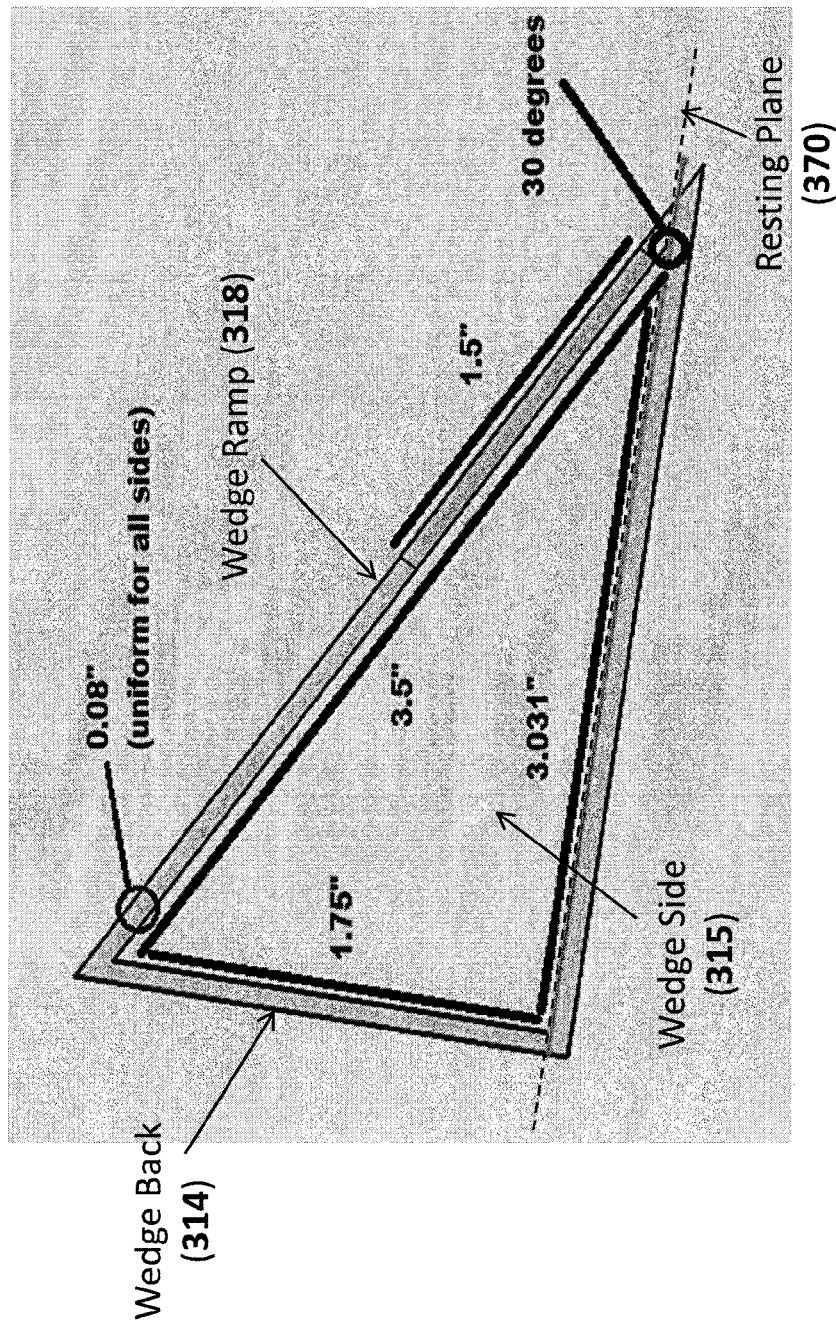
FIG. 16 is a technical diagram of the wedge back, side, and ramp from the deployment device according to FIG. 15 with demonstrative dimensional features.
Figure 17:
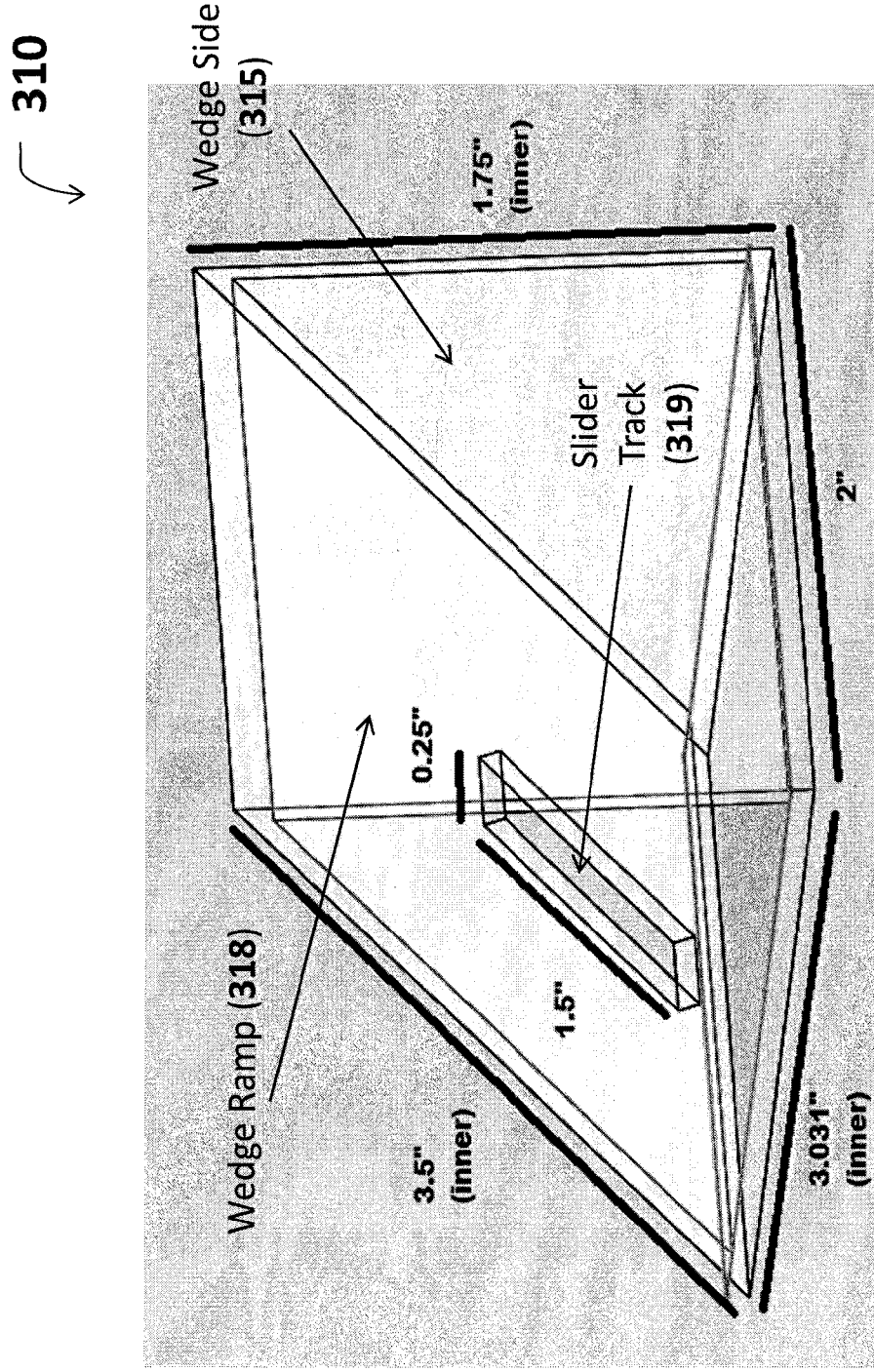
FIG. 17 is a perspective drawing of the wedge back, side, and ramp from the deployment device according to FIG. 15 with a slider track prominently displayed.

With reference to FIG. 16 and FIG. 17, exemplary dimensions for the wedge pieces 314, 315, 318, slider track 319, and an approximate 30 degree interface angle between wedge ramp 318 and a plane 370 upon which the device 310 rests, are illustrated.

Figure 18:
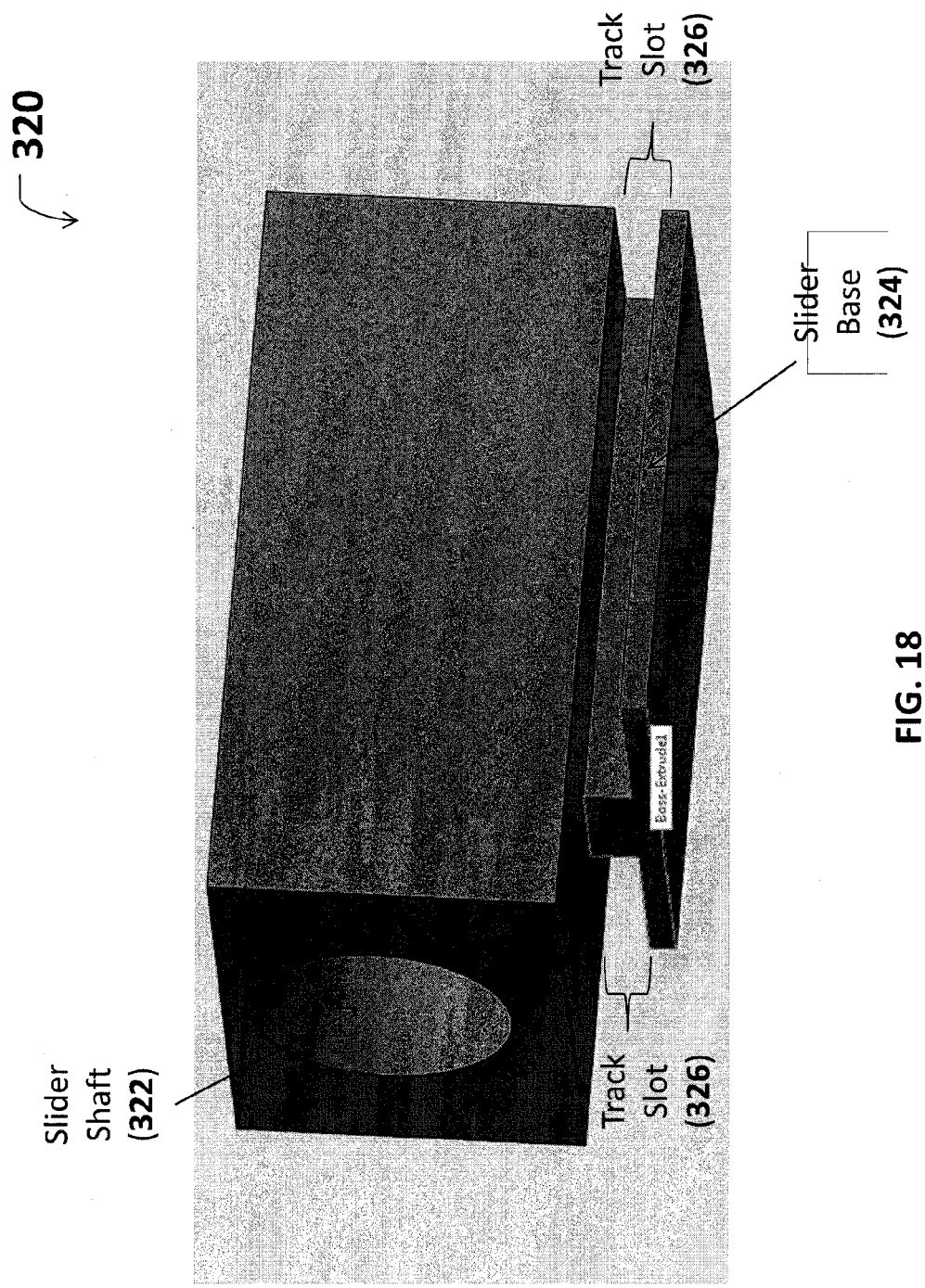
FIG. 18 is a perspective drawing of the slider of the deployment device according to FIG. 15.

With reference to FIG. 18, a slider 320 fit for deployment device 310 is illustrated. Slider 320 includes a slider base 324 with two track slots 326 for removably attaching slider 320 to slider track 319. Sider slots 326 enable slider 320 to translate along wedge ramp 318, similarly to slider 120 from deployment device 110 described in FIG. 2.

Figure 19:
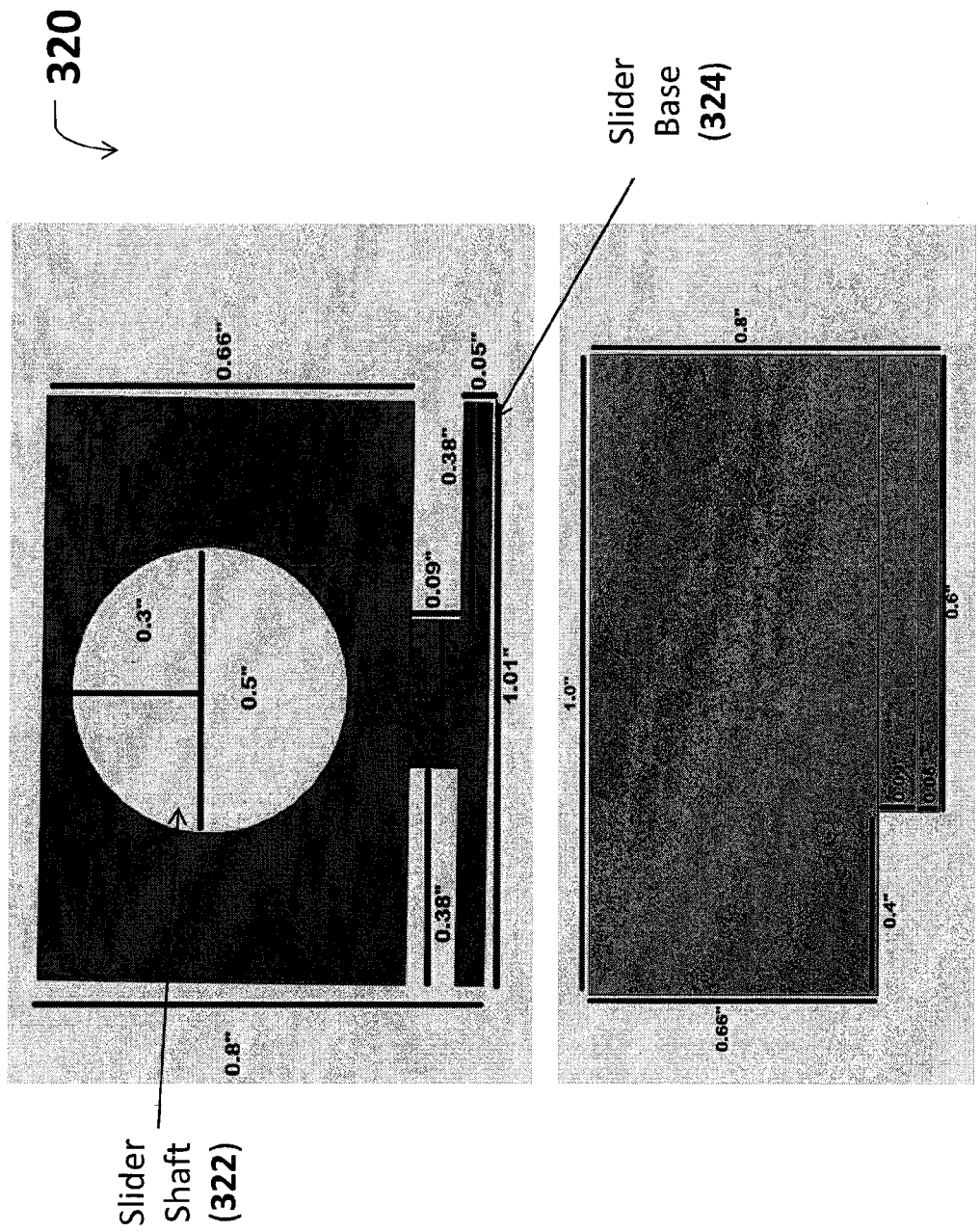
FIG. 19 is a technical diagram of the slider for the deployment device according to claim 15 with demonstrative dimensional figures.

With reference to FIG. 19, exemplary dimensions for slider 320 are illustrated. Slider 320 additionally includes a slider shaft 322 for inserting a lure 316 (not shown) with or without associated needle 317 (not shown). Exemplary dimensions of the slider shaft 322 are indicated.

Figure 20:
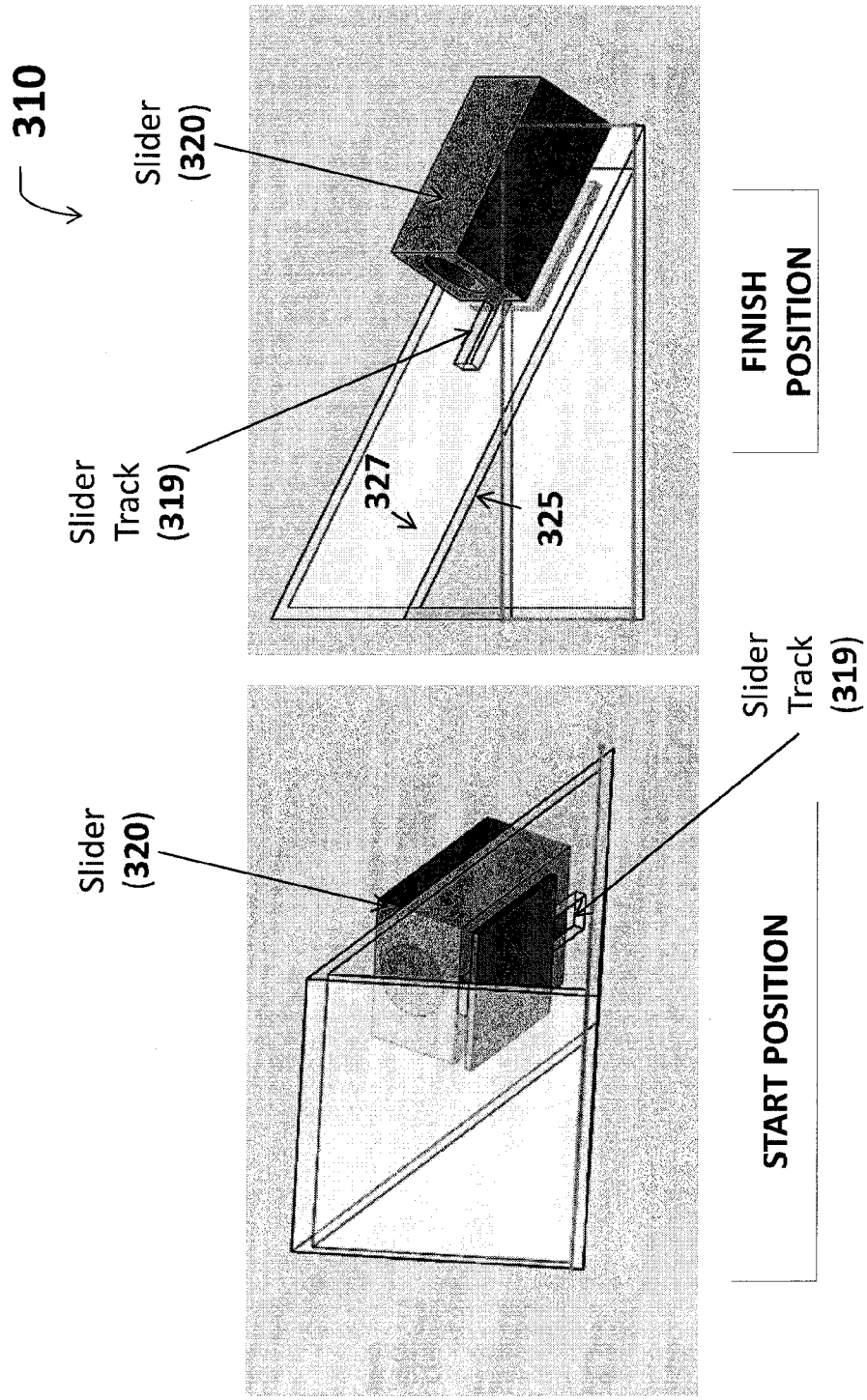
FIG. 20 is two perspective drawings of the deployment device according to FIG. 15 in showing a start and finish position.

With reference to FIG. 20, the deployment device 310 is shown in both a start and finish position, where if the slider 320 included a lure 316 with associated needle 317, device 310 would be fully deployed into the skin at the "finish position." To undeploy device 310, slider 320 would be translated along slider track 319 until it rests at the indicated "start position" configuration.

Figure 21:
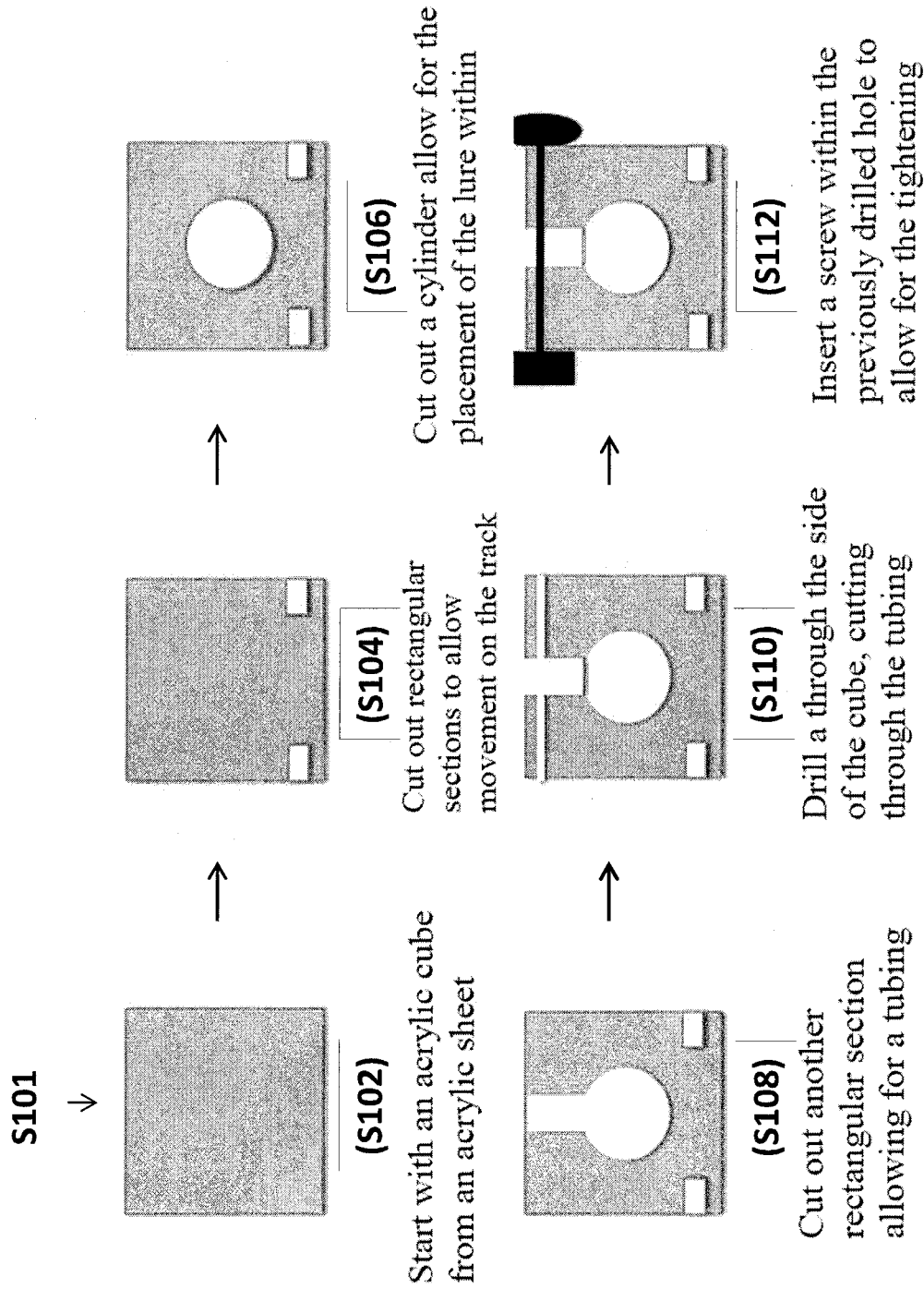
FIG. 21 is a manufacture process chart illustrating the different transformations an acrylic sheet undergoes when forming a slider for the deployment device according to FIG. 15.

With reference to FIG. 21, a method S100 for forming a low-cost acrylic slider starts at S101. At S102, an acrylic cube is cut from an acrylic sheet. This cube may be 1 inch cubed in dimensions. At S104, rectangular sections are cut from the acrylic cube to allow for movement on a track. At S106, a cylinder is cut from the acrylic cube to allow for placement of a lure within. The cylinder may be of radius 0.25 inches and cut centrally within the cube. At S108, a rectangular section is cut from the acrylic cube to allow for tubing. At S110, a hole is drilled through the side of the cube, cutting through the tubing. At S112, a screw is inserted through the previously made drilled hole to allow for tightening.

Figure 22:
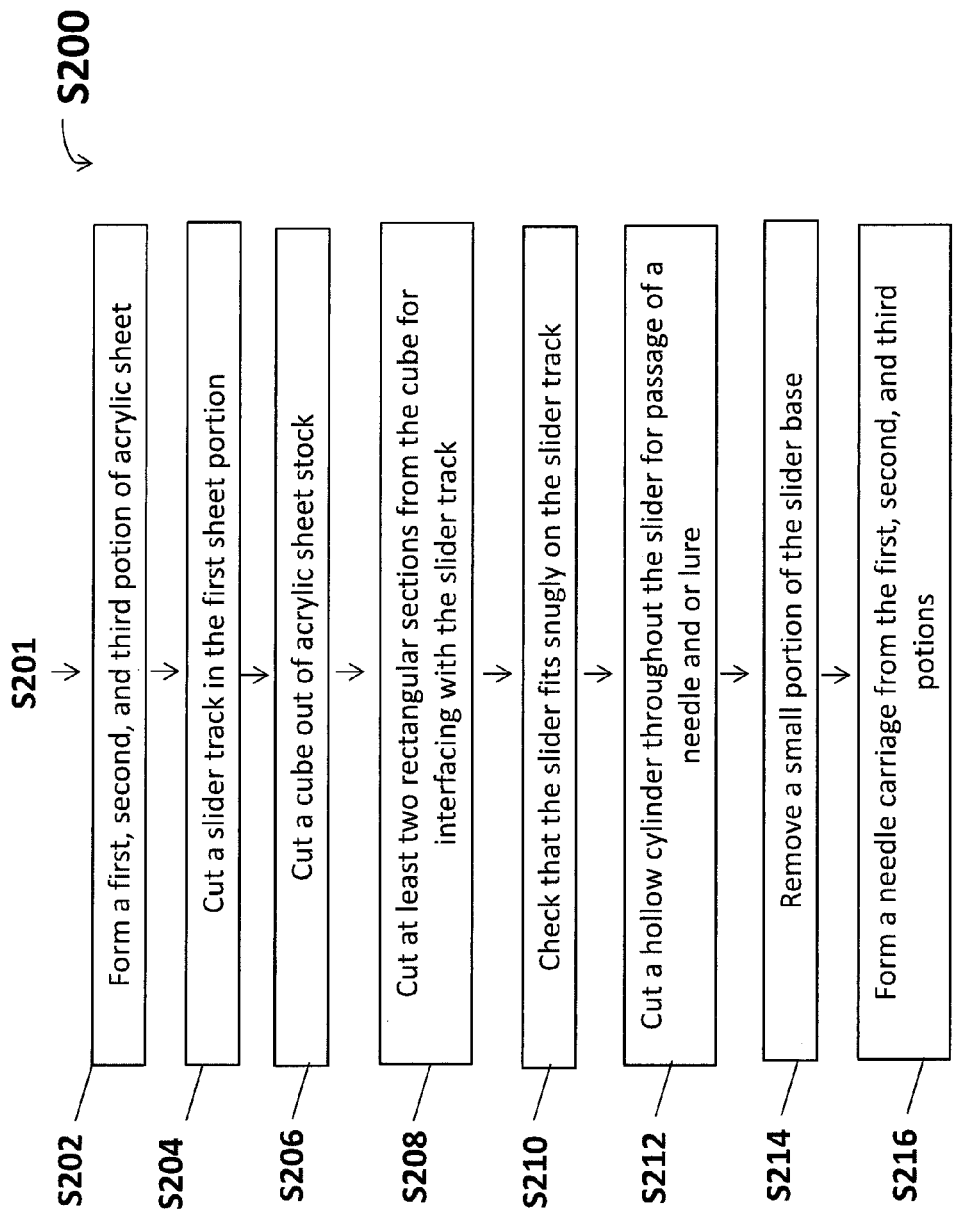
FIG. 22 is a flow chart of a method for forming the deployment device according to FIG. 15.

With reference to FIG. 22, a method S200 for forming a low-cost acrylic deployment device starts at S201. At S202, first, second, and third portions of acrylic sheet are cut from acrylic sheet stock. These sheets may represent the horizontal, vertical, and hypotenuse distances within a wedge with dimensions 3.031×2 inch+/−0.1 inch, 2 inch×1.75 inch +/−0.1 inch, and 3.5 inch×2 inch+/−0.1 inch, respectively. At S204, a slider track is cut in the first sheet portion. At S206, a cube is cut out of acrylic sheet stock. At S208, at least two rectangular sections are cut from the cube for interfacing with the slider track. At S210, a check is performed to see that the slider fits snugly on the track. At S212, a hollow cylinder is cut from the slider for passage of a lure and or needle. At S214, a small portion of the slider base is removed. Removal of this portion allows for the slider to reach its desired final position. Further modifications to the slider as disclosed in method S100 may be further incorporated into method S200. At S216, a needle carriage is formed from the first, second, and third acrylic sheet portions. This step may include maintaining an angle of approximately 30 degrees, +/−2 degrees, between acrylic sheet portions which form the smallest angle in the wedge needle carriage.

Figure 23:
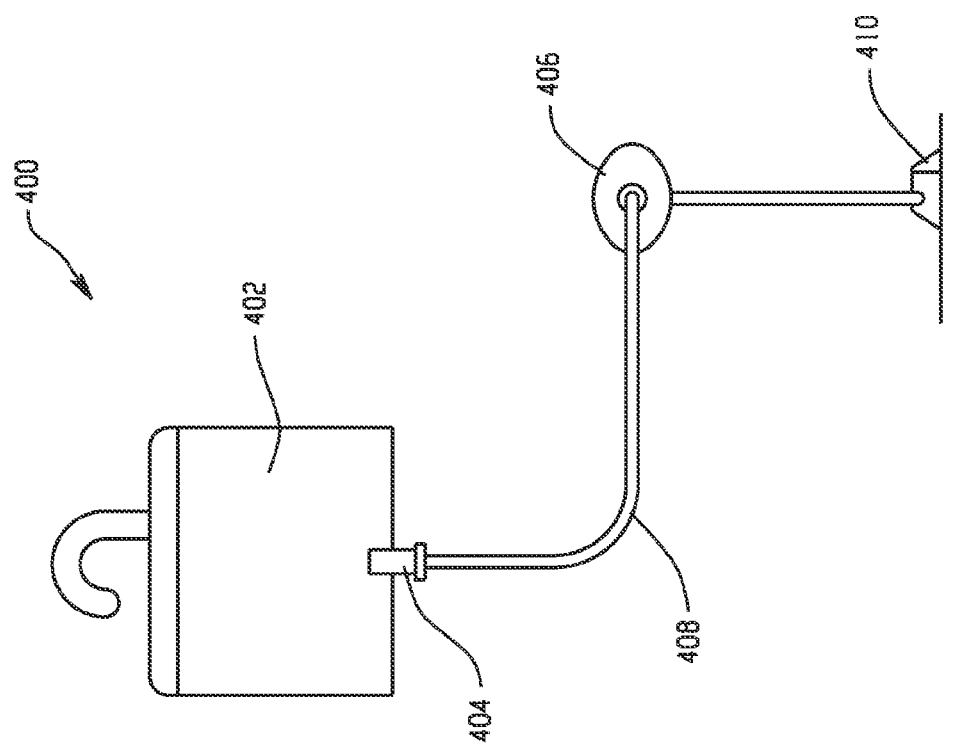
FIG. 23 is an overview drawing of a system for providing subcutaneous hydration according to a second exemplary embodiment.

With reference to FIG. 23, a system 400 for providing subcutaneous hydration according to a second exemplary embodiment. System 400 may be a fully integrated system which may provide for facile introduction of fluids into a subcutaneous space of human skin where they absorb into the microvasculature, providing volume replacement, without the need for a skilled operator to get intravenous access. System 400 includes an infusion bag 402 which provides hydration fluid to a deployment device 410 via tubing 408. Infusion bag 402 may include an integrated hanger, as illustrated, for hanging the bag 402 above the head of a patient to make use of gravitational forces in expelling fluids. Instructions may be located on infusion bag 402 to make operation of the system 400 easier to non-clinically trained administrators. The infusion bag 402 would include a measured amount, e.g. 500 mL, of isotonic crystalloid sterile fluids as known to one having ordinary skill in the art.

An iodine or similar prep kit (not shown) used for cleaning the skin before injection may be packaged with the infusion bag 402, with instructions for use of the iodine prep kit printed on the infusion bag 402.

The tubing 408 may be pre-connected to the infusion bag 402 to avoid potential confusion for non-skilled operators. The tubing 408 runs through a squeezable bulb 406 before passing to the deployment device 410. The squeezable bulb 406 acts as a priming chamber for flushing and priming the tube 408. The bulb 406 may contain a one-way valve. The tubing 408 may be pre-connected to a needle 417 integrated into the deployment device 410. The needle 417 may be a medium bore needle, e.g. 24 gauge, for general applications however can take on different dimensions as known to one having ordinary skill in the art when used for specialized applications.

Figure 24C:
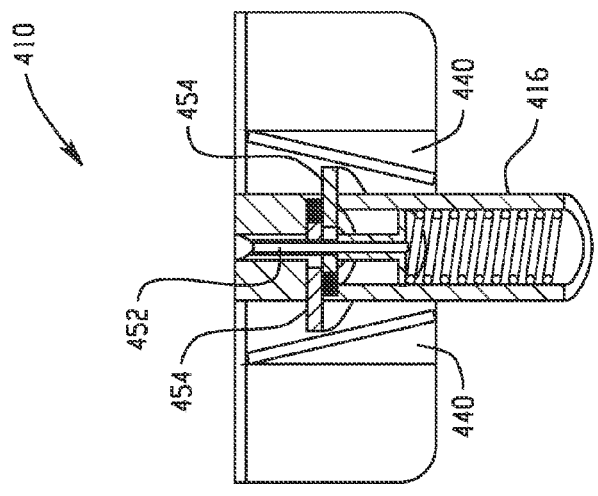
FIG. 24 is a bottom, rear, and top cutaway view drawing of an undeployed deployment device according to a third exemplary embodiment for use in the system of FIG. 23.
Figure 24B:
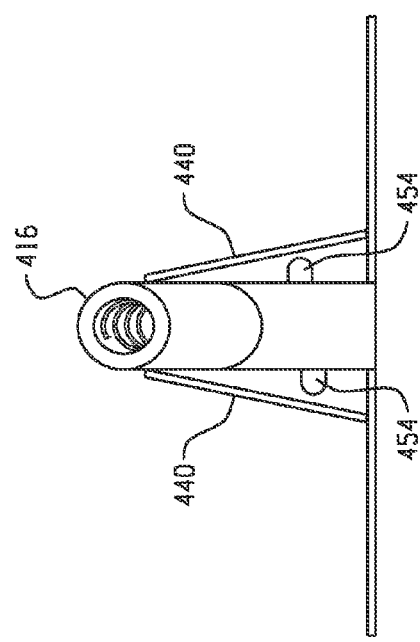
Figure 24A:
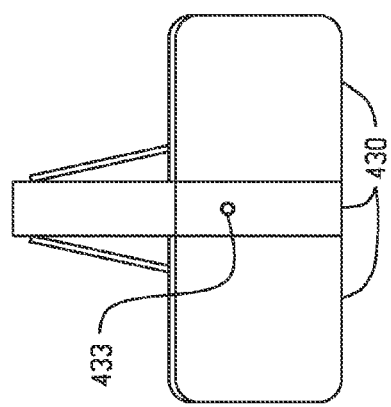

With reference to FIG. 24, the deployment device 410 in an undeployed mode is illustrated in a bottom (a), rear (b), and top (c) cutaway view. Deployment device 410 includes a base 430 for resting on the skin, which may be flexible or hinged depending on the material used to construct the base 430. The base 430 may include an antimicrobial material and/or water proof adhesive (not shown) for interfacing with the skin of a patient. A needle aperture 433 is located in the base 430 so that a needle 417 (not shown) located in a spring-loaded barrel 416 may pass through a needle slot 452 in barrel 416 and aperture in base 430 to puncture the skin once device 410 is placed in a deployed mode. The spring-loaded barrel 416 is also angled at an appropriate angle for safe injection, e.g. approximately 30 degrees. The barrel also houses the tubing 408 (not shown) which may be pre-connected to the needle 417. Wings 440 located on either side of barrel 416 are used for pushing the two sides of the base downward in order to pull up a tent of skin from a patient used for injection, and are further used to trigger actuators 454 which place device 410 in a deployed mode for injection activity.

One novel feature of deployment device 410 is the increased injection safety provided by barrel 430, wings 440, and actuators 454. The needle 417 will only deploy as a tent of skin is "pinched" up between the wings 440. This creates a space into which the needle is automatically and safely deployed once the wings 440 are squeezed enough to activate actuators 454 which unlock a firing mechanism 450 (described in FIG. 26 below) within the barrel to deploy the needle 417.

With reference to FIG. 25, the deployment device 410 in a fully deployed mode is illustrated in a (a) bottom and (b) rear cutaway view. Wings 440 have been adequately squeezed in order to engage the actuators 454. The needle 417 has been automatically deployed out of the aperture 433 located in the base 430 and can be seen coming out of the barrel 416 in the (b) rear cutaway view.

Figure 26:
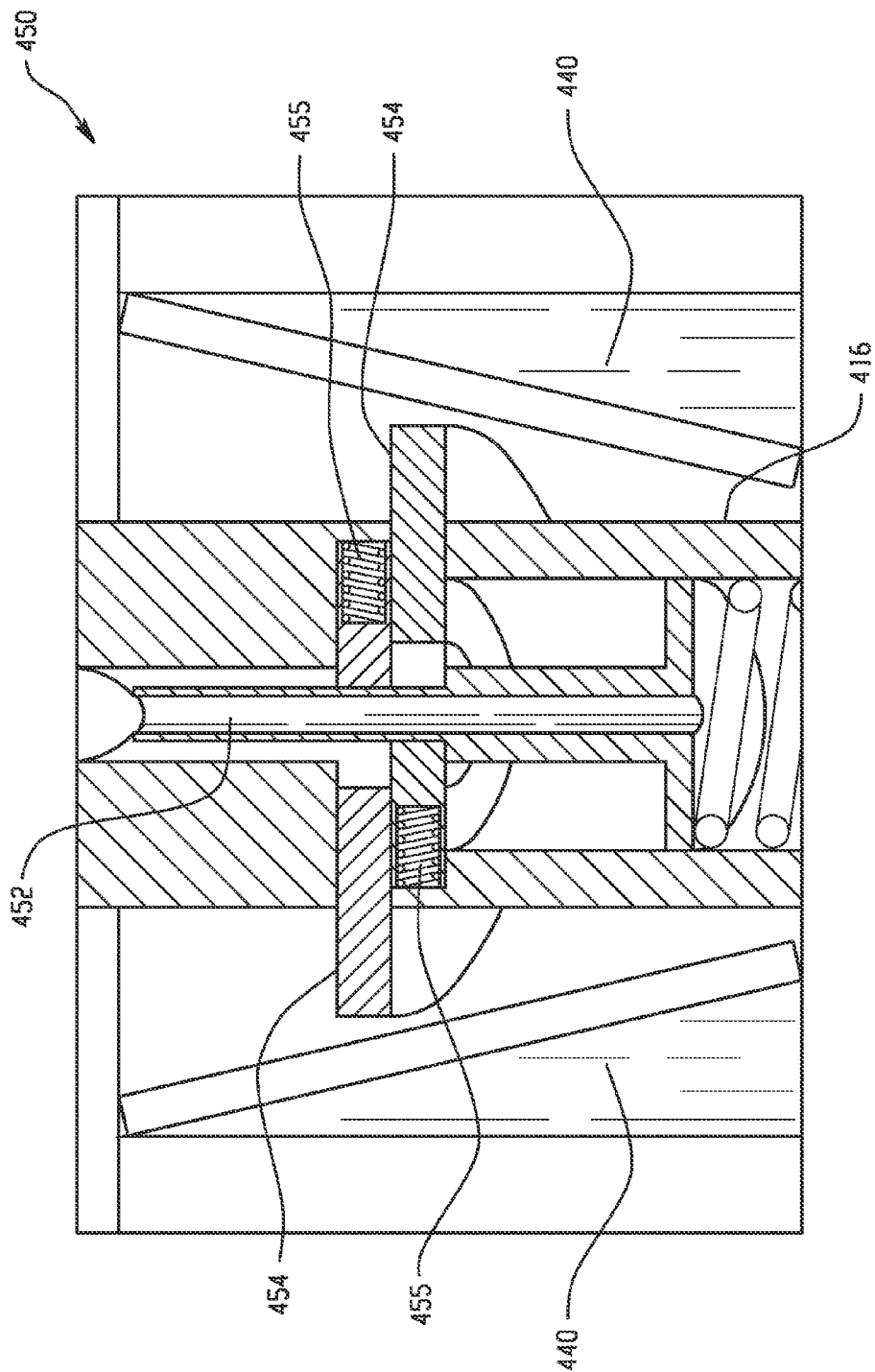
FIG. 26 is a drawing of the firing mechanism (under an undeployed state) of the deployment device according to FIG. 24.

With reference to FIG. 26, the firing mechanism 450 when the deployment device 410 is in the undeployed mode has been illustrated in greater detail. Actuators 454 may be connected to springs 455 which reside within barrel 416. When actuators 454 are sufficiently depressed by squeezing wings 440, the wings touch the actuators 454 and depress the actuators 454 and attached springs 455. As the actuators 454 are depressed, the needle slot 452 becomes unblocked so that a needle 417 (not shown) may be automatically deployed through the needle slot 452 to partially exit the barrel 416 and inject into the skin. Needle 417 is still partially held within the barrel 416, at least at a needle hub (not shown), to maintain the general angle of injection and to allow slight vertical pivot to accommodate skin movement.

Figure 27:
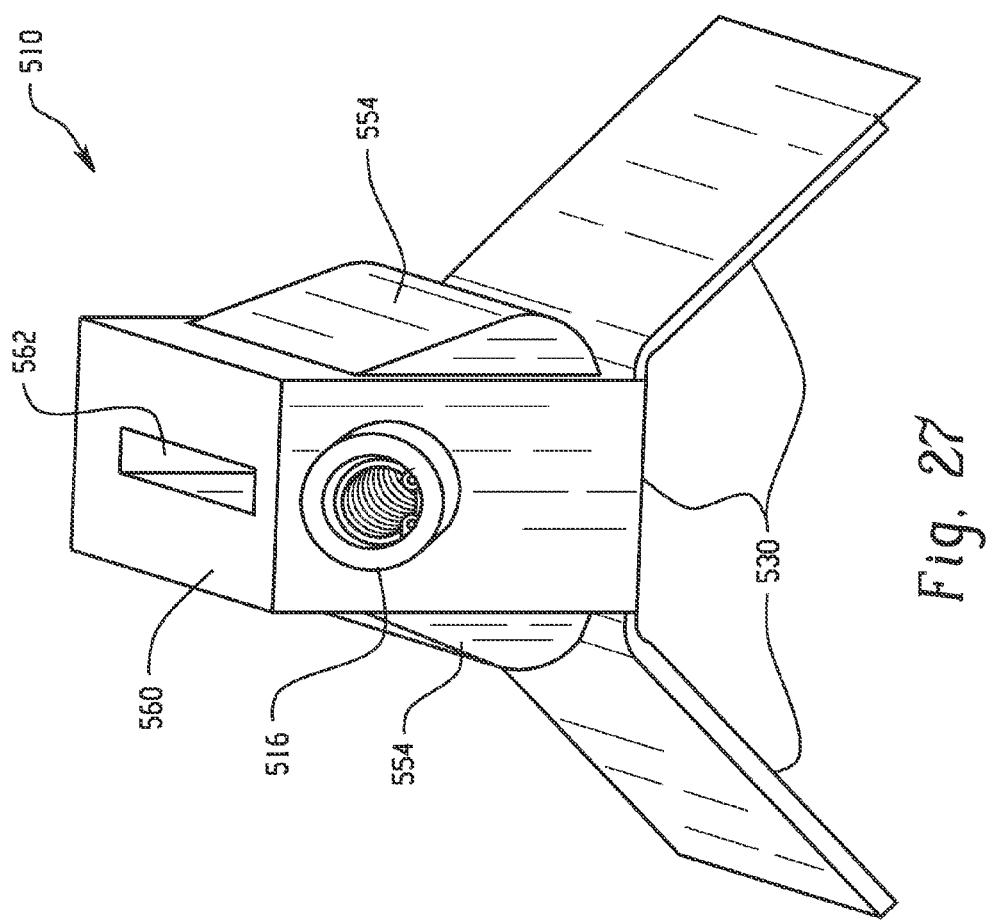
FIG. 27 is a 3D Model of a deployment device according to a fourth exemplary embodiment in a perspective view.

With reference to FIG. 27, a 3D model of a deployment device 510 according to a fourth exemplary embodiment is shown. Deployment device 510 is Modeled closely after device 410, however includes many notable improvements. Such improvements may include a more ergonomic shape for actuators 540 that resemble buttons and may promote squeezing. A casing 560 may be fit over a barrel 516 so that the barrel does not extrude far from the device. The casing 560 may include a slider track 562 used in conjunction with a slider 520 (not shown) to retract a needle 517 after it has been deployed. It should be noted that wings 540 (not shown) may emanate from near the top of the casing 560 and attach to the base 530. The wings 540 would function similar to the wings 440 in device 410, and could be used to depress actuators 554.

Figure 28:
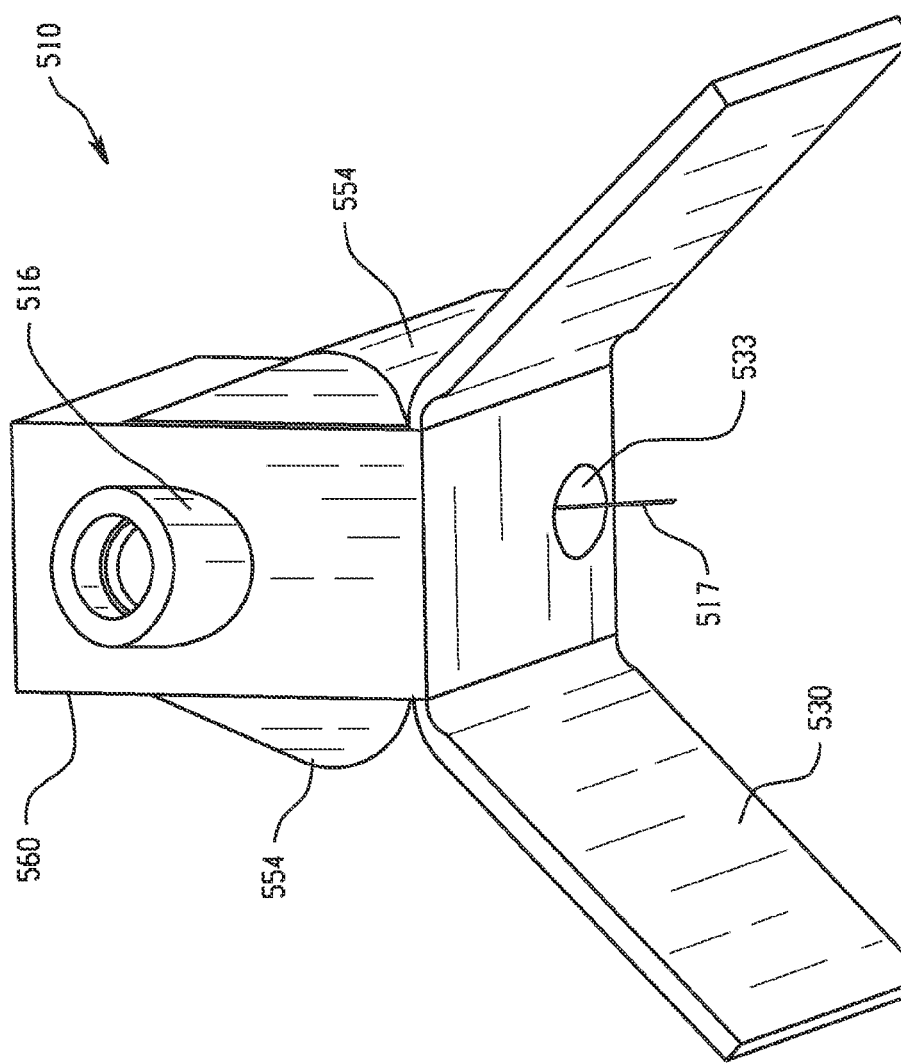
FIG. 28 is a bottom cutaway view of the 3D model of the deployment device according to FIG. 27. The needle appears to be deployed as it sticks out of the base.

With reference to FIG. 28, the deployment device 510 is shown in a deployed mode perspective view with the needle 517 protruding out of the barrel 516 through a needle aperture 533 located on base 530.

Figure 29:
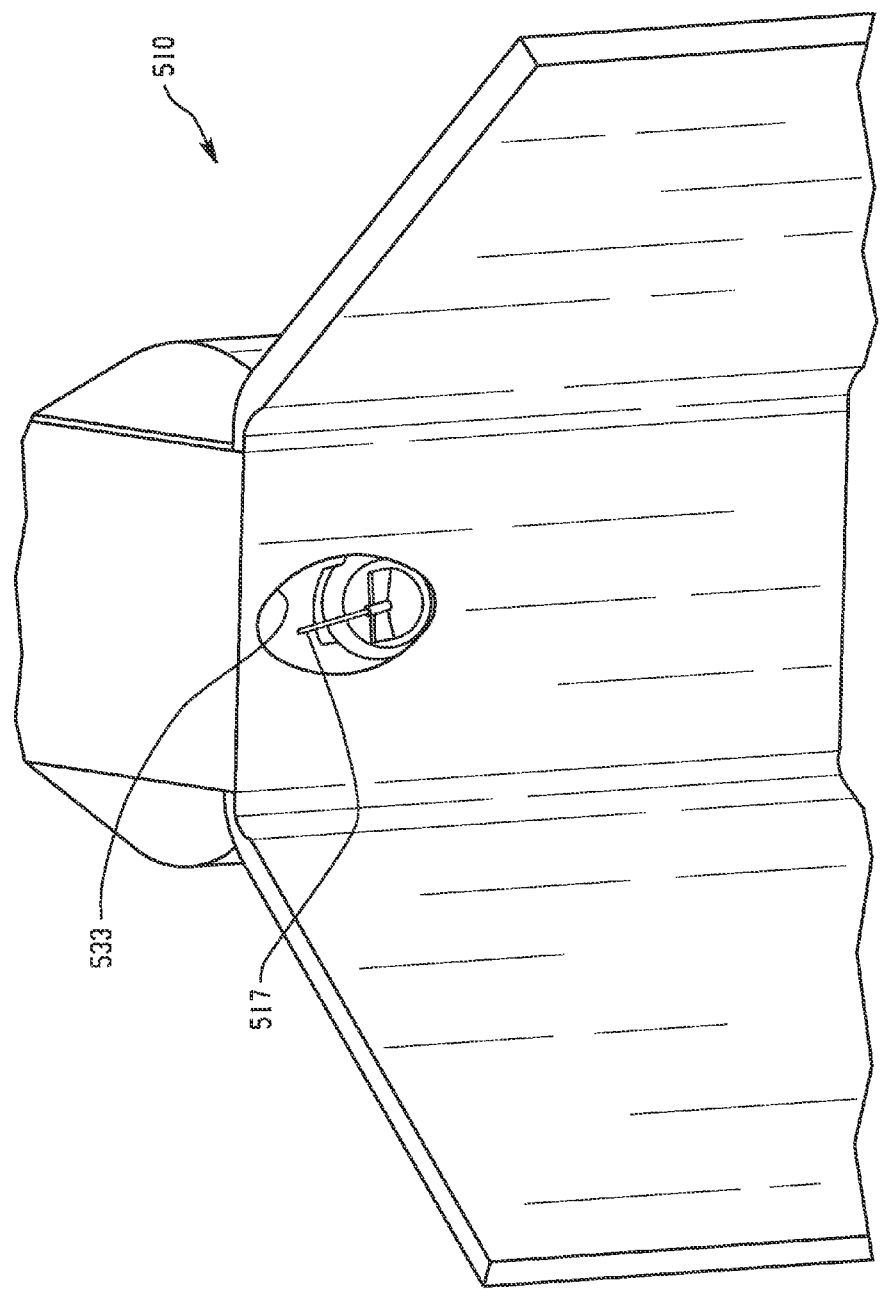
FIG. 29 is a close-up cutaway view of the base of the 3D model of the deployment device according to FIG. 27 showing an oblong needle aperture.

With reference to FIG. 29, the needle aperture 533 located on base 530 may be oblong or take on other beneficial shapes as appreciated by one having ordinary skill in the art to allow the needle 517 to pivot about the hub while deployed into the skin.

With reference to FIG. 30, needle 517 may be pre-connected to a tubing 508, both of which are partially housed within the barrel 516. The needle 517 once injected into dermis 534 may vary in position, however is held firm within the barrel 516 at least at the needle hub 519. Needle 517 position variance within aperture 533 may be due to expelled hydration fluid within a subcutaneous skin region pushing up against the needle. This concept was previously illustrated by increased force, $F_{skin}$, in FIG. 12. An oblong shape allows for needle 517 position variance without displacing needle 517 from the barrel 516 or causing unnecessary patient discomfort or tissue trauma.

With reference to FIG. 31, the slider track 562 is located above the spring-loaded barrel 516. An appropriate slider 520 (not shown) which fits along slider track 562 may include a snag or similar feature which engages or "catches" the spring 521 within the spring-loaded barrel 516 and retracts the needle 517 attached to the spring 521 when the slider 520 is translated along the slider track 562.

Figure 32:
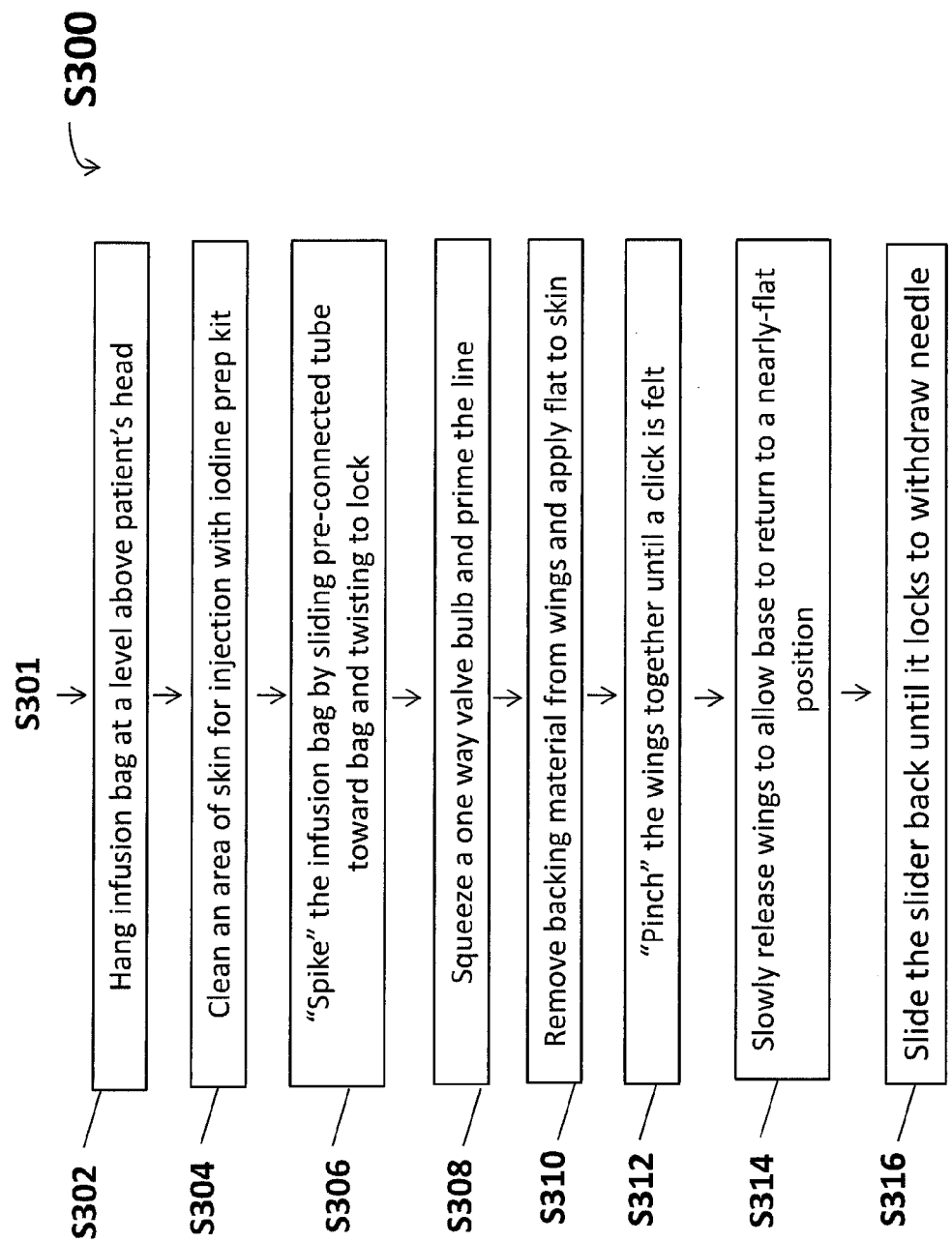
FIG. 32 is a method for providing subcutaneous hydration according to an exemplary embodiment.

With reference to FIG. 32, an exemplary method S300 for performing subcutaneous rehydration begins at S301. Method S300 may be performed with deployment device 410, 510 or other similar devices. At S302, an infusion bag is hung at a level above a patient's head. At S304, an area of skin is cleaned for injection with an iodine prep kit or the like. In one embodiment, the area of skin cleaned for injection is at least one of a back, thigh, or abdomen bodily area. At S306, the infusion bag is "spiked" by sliding a pre-connected tube towards the bag and twisting to lock. At S308, a one way valve bulb is squeezed to prime the tube. It should be noted that S306 or S308 may be performed in the alternative or in combination to prime the tube. At S310, backing material is removed from wings and applied flat to the skin. At S312, pinch the wings together until a click is felt. This action may pull up a tent of skin and automatically deploy a needle. At S314, wings are slowly released to allow base to return to a nearly-flat position. At S314, a slider is translated until locked in order to withdraw the needle from the patient.

It should be noted that while deployment devices 110, 210, 310, 410, 510, may be used as a secondary/temporizing means for rehydrating patients in the developing world with dehydrating diarrhea and emesis for whom 1) oral rehydration is either not possible (because of emesis, unresponsiveness, or young age) or not sufficient to offset fluid losses, and 2) access to clinically-trained personnel capable of administering intravenous fluids will be significantly delayed, there are also other significant applications. A device used in the third-world child rehydration setting may be the most basic, employing a smaller simple needle, and important further adaptions to the devices 110, 210, 310, 410, 510, may necessarily be contemplated for providing subcutaneous hydration in different settings.

For example, the deployment device 110, 210, 310, 410, 510 and/or systems 100, 400 may be adapted for otherwise extreme or military use on the battlefield where adults may face delays in receiving fluid replacement/resuscitation. Deviations from described devices may include using materials which can withstand excessive environmental temperatures for long periods of time and may be either wrapped in Ultraviolet (UV)-protective materials or manufactured from materials which degrade minimally in ultraviolet light. In order to avoid excessive solar heating of fluids in outdoor environments, the infusion bag 102, 402 may be light in color and nontransparent with the exception of a small, clear window for assessing turbidity of the fluid. The crystalloid fluids within infusion bag 102, 402 may also contain appropriately-dosed recombinant hyaluronidase, an enzyme which reversibly lowers the resistance to infusion of fluids into the subcutaneous space to allow more rapid infusion. The devices 110, 210, 310, 410, 510 may also include a larger bore needle. The devices may be manufactured such that a second or subsequent bag can be attached at entry point when the first infusion bag 102, 402 has been emptied.

Another adaption of the devices 110, 210, 310, 410, 510 may be for non-acute, developing world applications, e.g., the care of patients who require maintenance fluids in an institutional or home setting such as nursing home patients, hospice patients, and home care patients, patients who will have surgery the following day and who are allowed nothing by mouth). Deviations from the described devices 110, 210, 310, 410, 510 may include, in addition to an antibacterial preparation, placing an adhesive covering the portion of the base and/or wings that would also be impregnated with an emulsion of prilocaine and lidocaine local anesthetic. The same procedure for activating devices 410, 510 may be followed except a user would wait five minutes between application of the wings and pinch deployment of the needle. Additionally, an injection port may be included in the infusion bag 102, 402 for adding medications.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A deployment device (410, 510) for subcutaneous hydration, comprising:
   a base (430, 530) including a needle aperture (433, 533);
   a spring-loaded barrel (416, 516) attached to the base (430, 530) at an injection angle of 10 degrees to about 30 degrees, and including a needle (417, 517); and
   a firing mechanism (450, 550) within the barrel (416, 516) for deploying the needle (417, 517) from the barrel (416, 516), the mechanism comprising at one actuator (454, 554) attached to the barrel (416, 516) and connected to a spring (455) so as to block a needle slot (452), the at least one actuator (454, 554) being depressed to unblock the needle slot (452) and permit deployment of the needle;
   wherein the deployment device (410, 510) further includes at least one wing (440, 540) that attaches to the base (430, 530) for engaging the at least one actuator (454, 554), and
   wherein the at least one wing (440, 540) engages the at least one actuator (454, 554) by gripping or pinching the at least one wing (440, 540) against the barrel (416, 516).

2. The deployment device of claim 1, wherein the needle (417, 517) is partially held within the barrel (416, 516) after injection.

3. The deployment device of claim 1, wherein the aperture (433, 533) accommodates needle (417, 517) movement while the needle (417, 517) is at least partially stabilized by the barrel (416, 516).

4. The deployment device (410, 510) of claim 1, wherein the base (430, 530) includes at least one of an antimicrobial material and a waterproof adhesive.

5. The deployment device (410, 510) of claim 1, wherein the barrel (416, 516) at least partially encompasses a tubing (408, 508) operative to provide hydration fluid to the needle (417, 517).

6. The deployment device (410, 510) of claim 1, further including a casing (560) attached to the base (430, 530) which at least partially encompasses the barrel (417, 517).

7. The deployment device (410, 510) of claim 6, wherein the casing (560) includes a slider track (562) for retracting the needle (417, 517) within the spring-loaded barrel (416, 516).

8. A system (100, 400) for providing subcutaneous hydration, comprising:
   an infusion bag (102, 402) including a hydration fluid;
   a tubing (108, 408) removably attached to the infusion bag (102, 402) and at least partially encompassed by a valve (106, 406); and
   a deployment device (110, 410) attached to the tubing (108, 408);
   wherein the deployment device (110, 410) comprises:
      a base (430, 530) including a needle aperture (433, 533);
      a spring-loaded barrel (416, 516) attached to the base (430, 530) at an injection angle of 10 degrees to about 30 degrees, and including a needle (417, 517);
      a firing mechanism (450, 550) within the barrel (416, 516) for deploying the needle (417, 517) from the barrel (416, 516), the mechanism comprising at one actuator (454, 554) attached to the barrel (416, 516) and connected to a spring (455) so as to block a needle slot (452), the at least one actuator (454, 554) being depressed to unblock the needle slot (452) and permit deployment of the needle;
   wherein the deployment device (110, 510) further includes at least one wing (440, 540) that attaches to the base (430, 530) for engaging the at least one actuator (454, 554), and
      wherein the at least one wing (440, 540) engages the at least one actuator (454, 554) by gripping or pinching the at least one wing (440, 540) against the barrel (416, 516).

9. The system (100, 400) of claim 8, further comprising an adhesive base (132) for placement between a subcutaneous region (138) and the deployment device (110, 410).

10. The system (100, 400) of claim 9, wherein the adhesive base (132) includes an emulsion of at least one of prilocaine and lidocaine local anesthetic.

11. The system (100, 400) of claim 8, wherein the valve (106, 406) comprises a squeezable bulb (406) or a roller clamp (106).

* * * * *